United States Patent
Kim et al.

(10) Patent No.: US 7,867,631 B2
(45) Date of Patent: Jan. 11, 2011

(54) FLUORINE-CONTAINING COMPOUND AND ORGANIC LIGHT-EMITTING DEVICE EMPLOYING THE SAME

(75) Inventors: Young-Kook Kim, Suwon-si (KR); Seok-Hwan Hwang, Suwon-si (KR); Yoon-Hyun Kwak, Suwon-si (KR); Hye-Lim Lee, Suwon-si (KR)

(73) Assignee: Samsung Mobile Display Co., Ltd., Yongin-si (KR)

( * ) Notice: Subject to any disclaimer, the term of this patent is extended or adjusted under 35 U.S.C. 154(b) by 581 days.

(21) Appl. No.: 11/924,891

(22) Filed: Oct. 26, 2007

(65) Prior Publication Data

US 2008/0169755 A1    Jul. 17, 2008

(30) Foreign Application Priority Data

Jan. 15, 2007    (KR) .............. 10-2007-0004385

(51) Int. Cl.
*C07D 209/82*    (2006.01)
*H01L 51/54*    (2006.01)

(52) U.S. Cl. ............... 428/690; 428/917; 313/504; 313/506; 548/440

(58) Field of Classification Search ............... None
See application file for complete search history.

(56) References Cited

U.S. PATENT DOCUMENTS 4,666,810 A    5/1987 Umehara et al.

(Continued)

FOREIGN PATENT DOCUMENTS

JP    62-280850    12/1987

(Continued)

OTHER PUBLICATIONS

Office Action issued in corresponding Korean Patent Application No. 2007-0004385 dated Nov. 27, 2007.

(Continued)

*Primary Examiner*—Dawn Garrett

(74) *Attorney, Agent, or Firm*—Stein McEwen, LLP

(57) ABSTRACT

A fluorine-containing compound is represented by Formula 1 below:

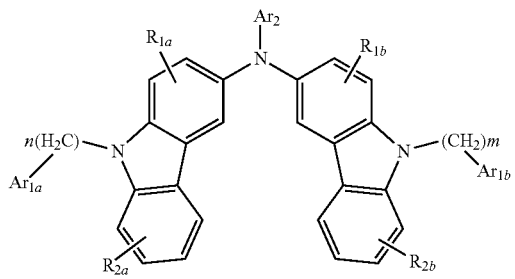

<Formula 1> wherein $R_{1a}$, $R_{1b}$, $R_{2a}$, and $R_{2b}$ are each independently a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 aryloxy group, a substituted or unsubstituted C4-C30 heteroaryl group, a substituted or unsubstituted C6-C30 condensed polycyclic group, a hydroxy group, halogen, a cyano group, or a substituted or unsubstituted amino group, and adjacent groups selected from $R_{1a}$, $R_{1b}$, $R_{2a}$, and $R_{2b}$ may join together to form a saturated or unsaturated carbon ring; n and m are each independently an integer of 0 to 5; $Ar_{1a}$ and $Ar_{1b}$ are each independently a C6-C30 aryl group which is unsubstituted or substituted by at least one fluorine or a C4-C30 heteroaryl group which is unsubstituted or substituted by at least one fluorine; and $Ar_2$ is a substituted or unsubstituted C6-C30 aryl group or a substituted or unsubstituted C2-C30 heteroaryl group. The fluorine-containing compound has good electrical characteristics and charge transport capability, and thus, is useful as a hole injection material, a hole transport material, and/or an emitting material for fluorescent or phosphorescent devices capable of producing light of a full spectrum of colors, including red, green, blue, and white. Thus, the fluorine-containing compound can be used to produce organic light-emitting devices with high efficiency, a low driving voltage, high brightness, and a long lifetime.

16 Claims, 3 Drawing Sheets

U.S. PATENT DOCUMENTS

| | | | |
|---|---|---|---|
| 5,756,248 A * | 5/1998 | Tanaka et al. | 430/83 |
| 6,465,115 B2 | 10/2002 | Shi et al. | |
| 6,596,415 B2 | 7/2003 | Shi et al. | |
| 7,431,997 B2 * | 10/2008 | Hwang et al. | 428/690 |
| 2006/0020136 A1 * | 1/2006 | Hwang et al. | 548/440 |
| 2006/0115680 A1 * | 6/2006 | Hwang et al. | 428/690 |
| 2009/0206745 A1 * | 8/2009 | Hwang et al. | 313/504 |
| 2010/0032656 A1 * | 2/2010 | Kwang et al. | 257/40 |

FOREIGN PATENT DOCUMENTS

| | | |
|---|---|---|
| JP | 25-01198 | 3/1996 |
| JP | 11-329734 | 11/1999 |
| JP | 2004-288380 | 10/2004 |

OTHER PUBLICATIONS

Adachi et al. "Endothermic Energy Transfer: A Mechanism for Generating Very Efficient High-Energy Phosphorescent Emission in Organic Materials." *Appl. Phys. Lett.*, 79, 2082-2084, 2001.

U.S. Appl. No. 11/926,364, filed Oct. 29, 2007, Kim et al., Samsung SDI Co., Ltd.

Search Report issued by Japanese Intellectual Property Office in Japanese Patent Application No. 2007-4385 on Sep. 29, 2008.

* cited by examiner

FIG. 1

| Second electrode |
| --- |
| One or more organic layers, at least one of which contains the fluorine-containing compound of Formula 1 |
| First electrode |

FIG. 2

| Second electrode |
| --- |
| Emitting layer |
| Hole injection layer |
| First electrode |

FIG. 3

| Second electrode |
| --- |
| Electron transport layer |
| Emitting layer |
| Hole injection/ hole transport layer |
| First electrode |

FIG. 4

| Second electrode |
| --- |
| Electron transport layer |
| Emitting layer |
| Hole transport layer |
| Hole injection layer |
| First electrode |

FIG. 5

| Second electrode |
| Electron injection layer |
| Electron transport layer |
| Emitting layer |
| Hole transport layer |
| Hole injection layer |
| First electrode |

FIG. 6

| Second electrode |
| Electron injection layer |
| Electron transport layer |
| Hole blocking layer |
| Emitting layer |
| Hole transport layer |
| Hole injection layer |
| First electrode |

FLUORINE-CONTAINING COMPOUND AND ORGANIC LIGHT-EMITTING DEVICE EMPLOYING THE SAME

CROSS-REFERENCE TO RELATED APPLICATIONS

This application claims the benefit of Korean Application No. 2007-4385, filed Jan. 15, 2007, in the Korean Intellectual Property Office, the disclosure of which is incorporated herein by reference.

BACKGROUND OF THE INVENTION

1. Field of the Invention

Aspects of the present invention relate to a fluorine-containing compound and an organic light-emitting device employing the same. More particularly, aspects of the present invention relate to a fluorine-containing compound that has electrical stability, good charge transport capability, and a high glass transition temperature and that can prevent crystallization. Aspects of the present invention further relate to an organic light-emitting device employing an organic layer including the fluorine-containing compound.

2. Description of the Related Art

Electroluminescent (EL) devices are self-emitting devices that have advantages such as a wide viewing angle, good contrast, and a rapid response time. EL devices are classified into inorganic EL devices, which include an emitting layer formed of an inorganic compound, and organic EL devices, which include an emitting layer formed of an organic compound. Organic EL devices show better brightness, driving voltage, and response speed characteristics compared to inorganic EL devices, and can create polychromatic light. Thus, extensive research into organic EL devices has been conducted.

Generally, organic light-emitting devices have a stacked structure including an anode, an organic light-emitting layer, and a cathode. A hole injection/transport layer or an electron injection layer may be further disposed between the anode and the organic light-emitting layer or between the organic light-emitting layer and the cathode to form an anode/hole transport layer/organic light-emitting layer/cathode structure, an anode/hole transport layer/organic light-emitting layer/electron transport layer/cathode structure, or the like.

A polyphenyl hydrocarbon and an anthracene derivative have been described as material for forming a hole transport layer (U.S. Pat. Nos. 6,596,415 and 6,465,115).

However, organic light-emitting devices including hole transport layers formed of currently available hole transport layer materials have disadvantages in terms of lifetime, efficiency, and power consumption characteristics, and thus, there is room for improvement in conventional organic EL devices.

SUMMARY OF THE INVENTION

Aspects of the present invention provide a fluorine-containing compound that has electrical stability, good charge transport capability, and a high glass transition temperature, can prevent crystallization, and is suitable as an organic layer material for fluorescent or phosphorescent devices capable of producing light of a full spectrum of colors, including red, green, blue, and white.

Aspects of the present invention also provide an organic light-emitting device showing high efficiency, a low driving voltage, high brightness, and long lifetime, by virtue of employing an organic layer including the fluorine-containing compound.

According to an aspect of the present invention, there is provided a fluorine-containing compound represented by Formula 1 below:

<Formula 1>

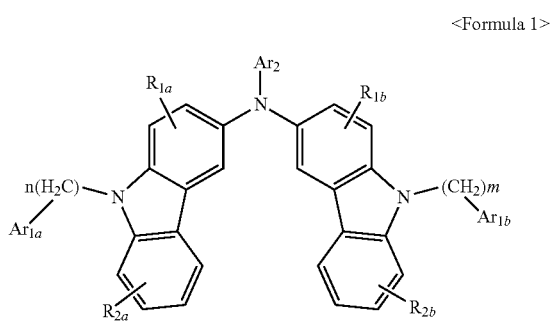

wherein $R_{1a}$, $R_{1b}$, $R_{2a}$, and $R_{2b}$ are each independently a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 aryloxy group, a substituted or unsubstituted C4-C30 heteroaryl group, a substituted or unsubstituted C6-C30 condensed polycyclic group, a hydroxy group, halogen, a cyano group, or a substituted or unsubstituted amino group, and adjacent groups selected from $R_{1a}$, $R_{1b}$, $R_{2a}$, and $R_{2b}$ may join together to form a saturated or unsaturated carbon ring;

n and m are each independently an integer of 0 to 5;

$Ar_{1a}$ and $Ar_{1b}$ are each independently a C6-C30 aryl group which is unsubstituted or substituted by at least one fluorine or a C4-C30 heteroaryl group which is unsubstituted or substituted by at least one fluorine; and $Ar_2$ is a substituted or unsubstituted C6-C30 aryl group or a substituted or unsubstituted C2-C30 heteroaryl group.

According to another aspect of the present invention, there is provided an organic light-emitting device including one or more organic layers interposed between a first electrode and a second electrode, wherein at least one of the one or more organic layers includes the fluorine-containing compound.

The organic layer may be a hole injection layer, a hole transport layer, or a single layer having hole injection capability and hole transport capability, or may be an emitting layer.

A fluorine-containing compound according to aspects of the present invention has good electrical characteristics and charge transport capability, and thus, is useful as a hole injection material, a hole transport material, and/or an emitting material for fluorescent or phosphorescent devices capable of producing light of a full spectrum of colors, including red, green, blue, and white, thereby making it possible to produce an organic light-emitting device with high efficiency, a low driving voltage, high brightness, and long lifetime.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 1 through 7 are views illustrating organic light-emitting devices according to embodiments of the present invention.

DETAILED DESCRIPTION OF THE EMBODIMENTS

Figure 7:
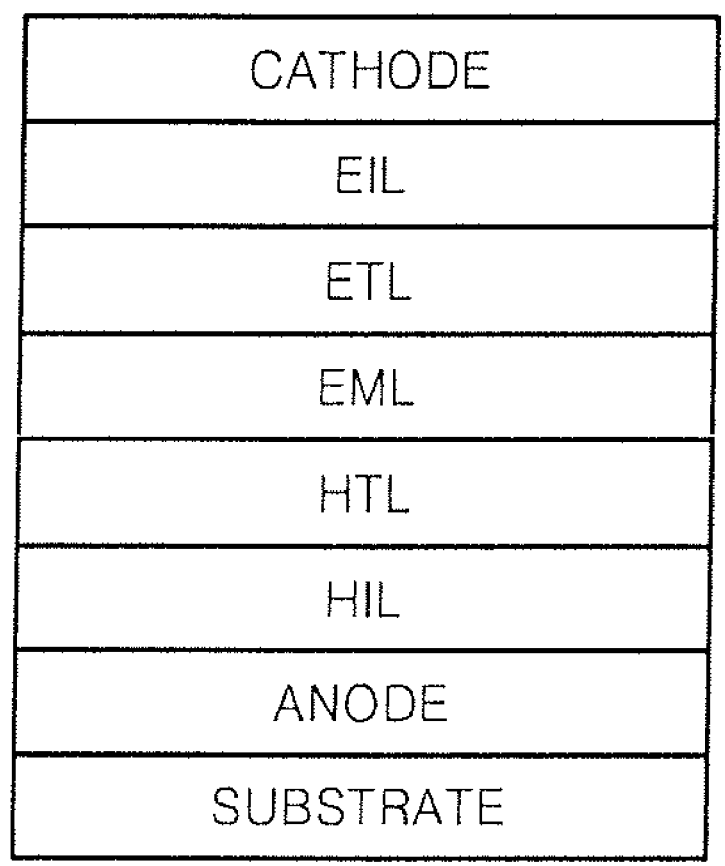

Reference will now be made in detail to the present embodiments of the present invention, examples of which are illustrated in the accompanying drawings, wherein like reference numerals refer to the like elements throughout. The embodiments are described below in order to explain the present invention by referring to the figures.

Aspects of the present invention provide a novel fluorine-containing compound represented by Formula 1 below, and an organic light-emitting device employing the compound as a material for forming an organic layer, such as a hole injection layer, a hole transport layer, or an emitting layer.

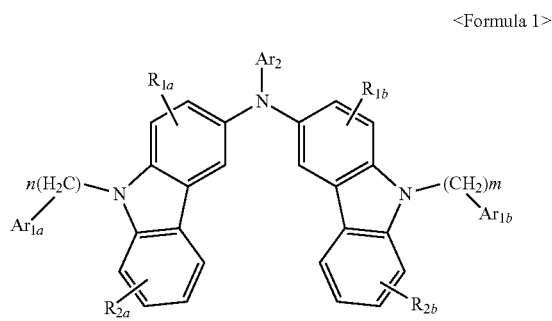

<Formula 1> wherein $R_{1a}$, $R_{1b}$, $R_{2a}$, and $R_{2b}$ are each independently a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 aryloxy group, a substituted or unsubstituted C4-C30 heteroaryl group, a substituted or unsubstituted C6-C30 condensed polycyclic group, a hydroxy group, halogen, a cyano group, or a substituted or unsubstituted amino group, and adjacent groups selected from $R_{1a}$, $R_{1b}$, $R_{2a}$, and $R_{2b}$ may join together to form a saturated or unsaturated carbon ring; and $Ar_{1a}$ and $Ar_{1b}$ are each independently a C6-C30 aryl group which is unsubstituted or substituted by at least one fluorine or a C4-C30 heteroaryl group which is unsubstituted or substituted by at least one fluorine and $Ar_2$ is a substituted or unsubstituted C6-C30 aryl group or a substituted or unsubstituted C2-C30 heteroaryl group. In the fluorine-containing compound represented by Formula 1, at least one of $R_{1a}$, $R_{1b}$, $R_{2a}$, and $R_{2b}$ is a fluorine or is substituted with at least one fluorine and/or at least one of $Ar_{1a}$, $Ar_{1b}$ or $Ar_2$ is substituted with at least one fluorine. As a non-limiting example, at least two of $R_{1a}$, $R_{1b}$, $R_{2a}$, $R_{2b}$, $Ar_{1a}$, $Ar_{1b}$ or $Ar_2$ may be substituted with one or more fluorines.

An aryl compound having carbon atoms of 13 or more may be difficult to be deposited due to a relatively high molecular weight. Thus, $Ar_{1a}$ and $Ar_{1b}$ may be each independently selected from an at least one fluorine-substituted C6-C12 aryl compound and an at least one fluorine-substituted C4-C12 heterocyclic compound.

As non-limiting examples, $Ar_{1a}$ and $Ar_{1b}$ may be each independently an at least one fluorine-substituted phenyl, biphenyl, or naphthalene group. In other words, $Ar_{1a}$ and $Ar_{1b}$ may each be a phenyl, biphenyl or naphthalene group that is substituted by one or more fluorine atoms, and $Ar_{1a}$ and $Ar_{1b}$ may be alike or different. For example, $Ar_{1a}$ and $Ar_{1b}$ may be each independently selected from materials having structures represented in Formula 2 below, but are not limited to:

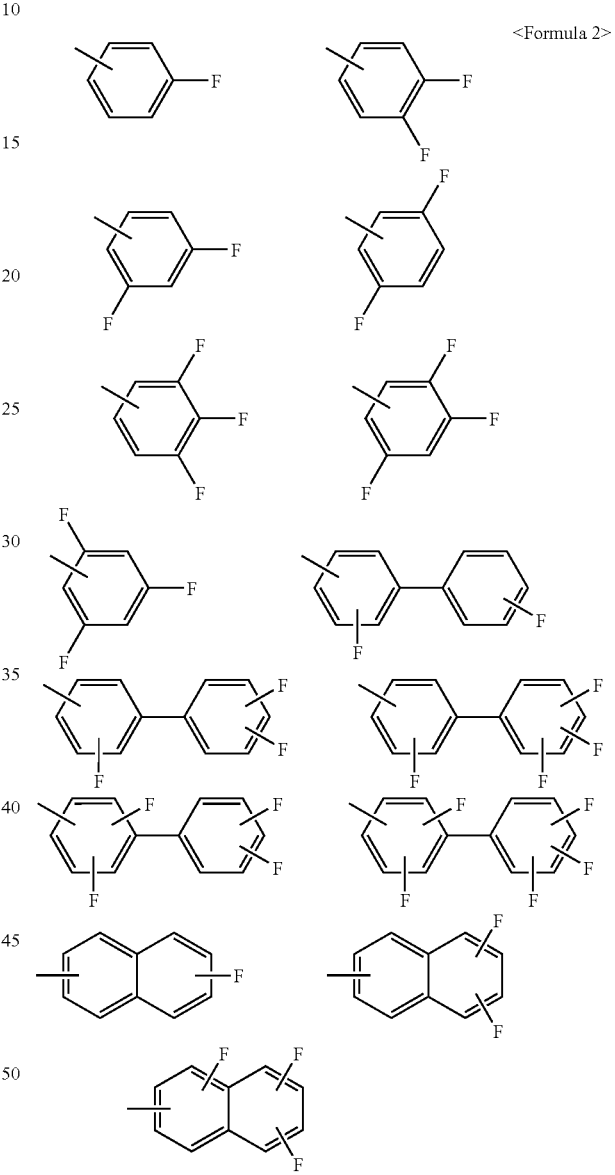

<Formula 2>

In Formula 1, $Ar_2$ is a substituted or unsubstituted C6-C30 aryl group or a substituted or unsubstituted C2-C30 heteroaryl group. As a non-limiting example, $Ar_2$ may be a phenyl group, a lower alkylphenyl group, a lower alkoxyphenyl group, a cyanophenyl group, a phenoxyphenyl group, a halophenyl group, a naphthyl group, a lower alkylnaphthyl group, a lower alkoxynaphthyl group, a cyanonaphthyl group, a halonaphthyl group, a fluorenyl group, a carbazolyl group, a lower alkylcarbazolyl group, a biphenyl group, a lower alkylbiphenyl group, a lower alkoxybiphenyl group, or a pyridyl group. The above-described lower alkyl and lower alkoxy may have 1-5 carbon atoms. As a specific, non-limiting example, Ar$_2$ may be a monocyclic, bicyclic, or tricyclic aryl group selected from a fluorenyl group, a carbazolyl group, a phenyl group, a naphthyl group, and a biphenyl group; or a monocyclic, bicyclic, or tricyclic aryl group selected from a fluorenyl group, a carbazolyl group, a phenyl group, a naphthyl group, and a biphenyl group, which is substituted by 1-3 substituents, preferably one substituent, selected from C1-C3 lower alkyl, C1-C3 lower alkoxy, cyano, phenoxy, phenyl, and halogen.

Examples of Ar$_2$ include, but are not limited to, a phenyl group, an ethylphenyl group, an ethylbiphenyl group, o-, m-, and p-fluorophenyl groups, a dichlorophenyl group, a dicyanophenyl group, a trifluoromethoxyphenyl group, o-, m-, and p-tolyl groups, a mesytyl group, a phenoxyphenyl group, a dimethylphenyl group, a (N,N'-dimethyl)aminophenyl group, a (N,N'-diphenyl)aminophenyl group, a pentalenyl group, a naphthyl group, a methylnaphthyl group, an anthracenyl group, an azulenyl group, a heptalenyl group, an acetonaphthalenyl group, a fluorenyl group, an anthraquinolyl group, a phenanthryl group, a triphenylene group, a pentaphenyl group, a hexaphenyl group, and a carbazolyl group.

In Formula 1, n and m are each independently an integer of 0 to 5. As a non-limiting example, n and m may be each independently 0, 1, or 2.

Definition of representative groups in the formulae used herein will now be described.

Examples of an unsubstituted C1-C20 alkyl group include methyl, ethyl, propyl, isobutyl, sec-butyl, pentyl, iso-amyl, and hexyl. At least one hydrogen atom of the alkyl group may be substituted by a halogen atom, a hydroxy group, a nitro group, a cyano group, an amino group, an amidino group, hydrazine, hydrazone, a carboxyl group or its salt, a sulfonyl group or its salt, a phosphonyl group or its salt, a C1-C30 alkyl group, a C1-C30 alkenyl group, a C1-C30 alkynyl group, a C6-C30 aryl group, a C7-C30 arylalkyl group, a C2-C20 heteroaryl group, or a C3-C30 heteroarylalkyl group.

Examples of an unsubstituted C1-C20 alkoxy group include methoxy, ethoxy, phenyloxy, cyclohexyloxy, naphthyloxy, isopropyloxy, and diphenyloxy. At least one hydrogen atom of the alkoxy group may be substituted by the same substituents as those recited in the above definition of the alkyl group.

The term "unsubstituted C6-C20 aryl group,", which is used alone or in combination, refers to an aromatic carbocyclic system containing one or more rings. The rings may be attached to each other as pendant groups or may be fused. At least one hydrogen atom of the aryl group may be substituted by the same substituents as those recited in the above definition of the alkyl group.

The aryl group may be a phenyl group, an ethylphenyl group, an ethylbiphenyl group, an o-, m-, or p-fluorophenyl group, a dichlorophenyl group, a dicyanophenyl group, a trifluoromethoxyphenyl group, an o-, m-, or p-tolyl group, an o-, m-, or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a methylnaphthyl group, an anthracenyl group, an azulenyl group, a heptalenyl group, an acetonaphthalenyl group, a phenalenyl group, a fluorenyl group, an anthraquinolyl group, a methylanthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, etc.

Examples of an unsubstituted aryloxy group include phenyloxy, naphthyleneoxy, and diphenyloxy. At least one hydrogen atom of the aryloxy group may be substituted by the same substituents as those recited in the above definition of the alkyl group.

The term "an unsubstituted heteroaryl group" as used herein refers to a monovalent or bivalent monocyclic or bicyclic aromatic organic compound of 6-30 carbon atoms containing one, two or three heteroatoms selected from N, O, P, and S. At least one hydrogen atom of the heteroaryl group may be substituted by the same substituents as those recited in the above definition of the alkyl group.

Examples of the heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, etc.

A fluorine-containing compound of Formula 1 has a high glass transition temperature or melting temperature due to a rigid carbazole group, thereby increasing the resistance to Joule's heat generated in an organic layer, between organic layers, or between an organic layer and a metal electrode when emitting light under an electric field and has a high tolerance to high temperature conditions. Moreover, the amorphous characteristics are increased due to an alkylaryl group introduced to the N-position of the carbazole, and thus, crystallization is prevented, thereby improving lifetime characteristics.

In particular, due to the characteristics of fluorine, which can withdraw electrons, the substituent(s) containing at least one fluorine in $Ar_{1a}$ and $Ar_{1b}$ of Formula 1 can trap electrons. Generally, when a hole transport material is exposed to an influx of electrons or an electron transport material is exposed to an influx of holes, device characteristics may be lowered. Thus, in order to produce long-lifetime devices, it is desirable to use a material that is capable of trapping excess holes or electrons that may be injected into an electron transport layer or a hole transport layer through an emitting layer, to stabilize the hole transport layer or the electron transport layer. A fluorine-containing compound of Formula 1 has a fluoro group capable of trapping excess electrons, and thus, can protect or stabilize a hole transport material from an influx of electrons, thereby improving device characteristics, resulting in an increase in device lifetime. When a fluorine-containing compound of Formula 1 is used as a hole injection layer material, a hole transport layer material, an emitting material, or a host material of an emitting layer in an organic light-emitting device, it is advantageous to increase brightness and to achieve light emission for a long time. In particular, since two or more rigid carbazole groups substituted by fluorine are contained in the molecule of a fluorine-containing compound of the present invention, the above-described effects can be more easily attained.

An organic light-emitting device according to aspects of the present invention exhibits high durability during storage and driving since the phenylcarbazole derivative used in organic light-emitting device according to aspects of the present invention has a high glass transition temperature (Tg). Fluorine-containing compounds represented by Formula 1 can be used as hole injection materials, hole transport materials, or emitting materials. Examples of a fluorine-containing compound of Formula 1 include, but are not limited to, compounds 1-96 represented in Formula 3 below:

<Formula 3>
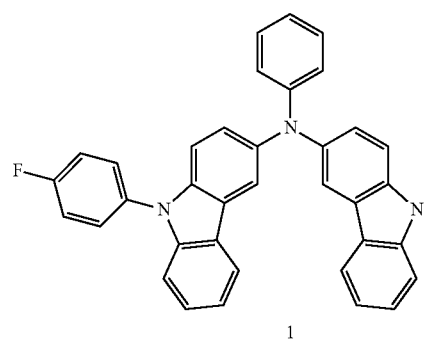
1
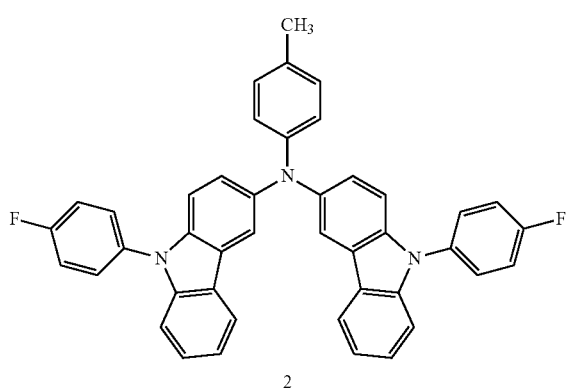
2
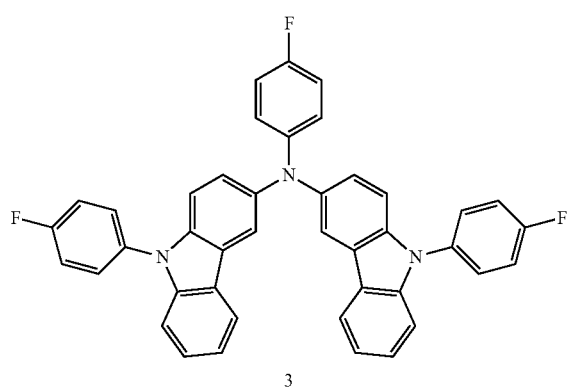
3
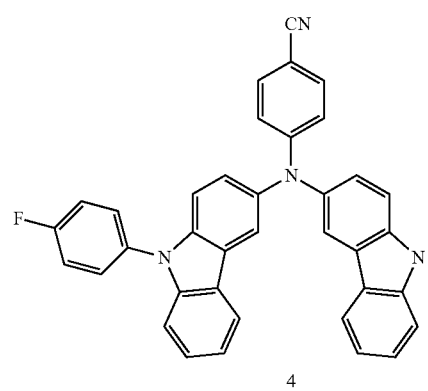
4
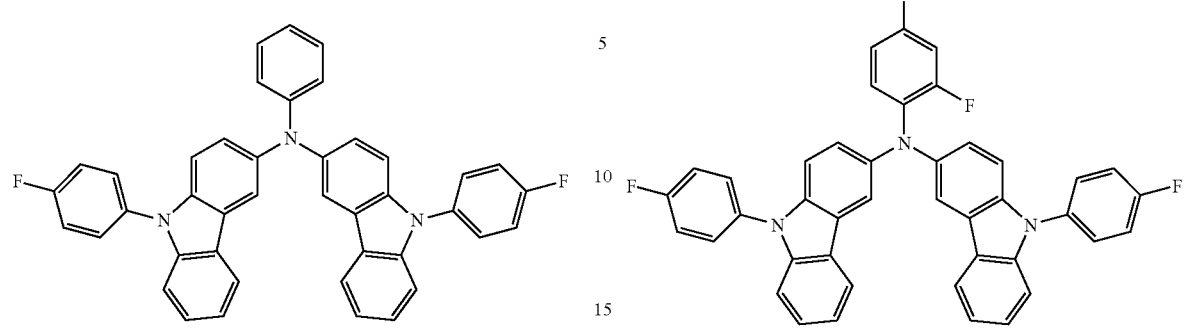
5
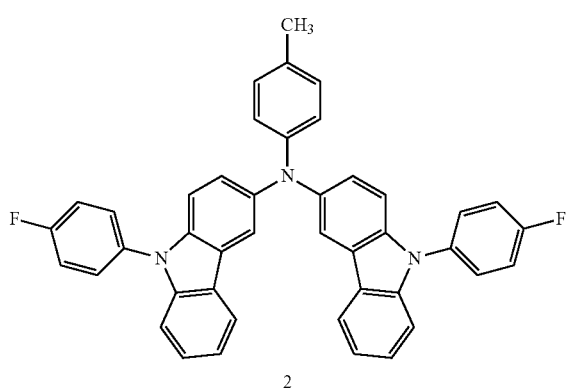
6
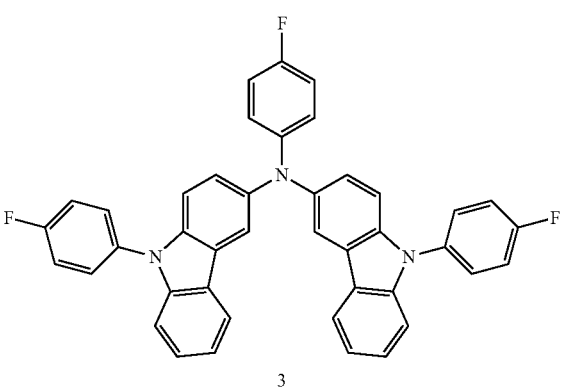
7
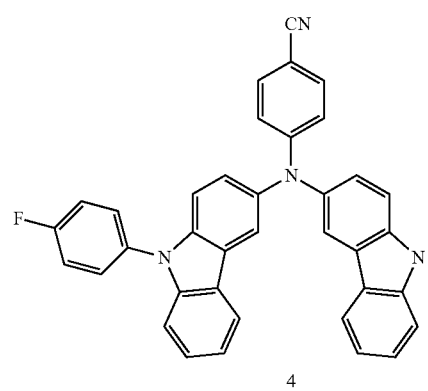
8

-continued
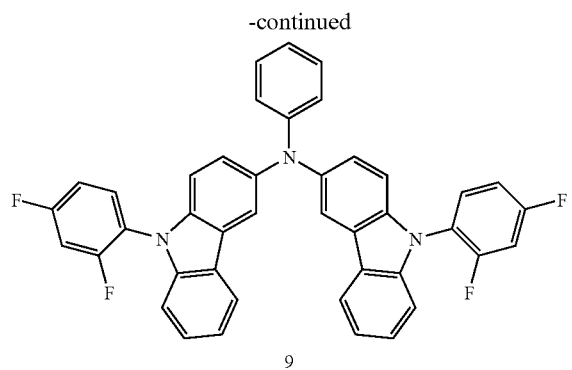
9
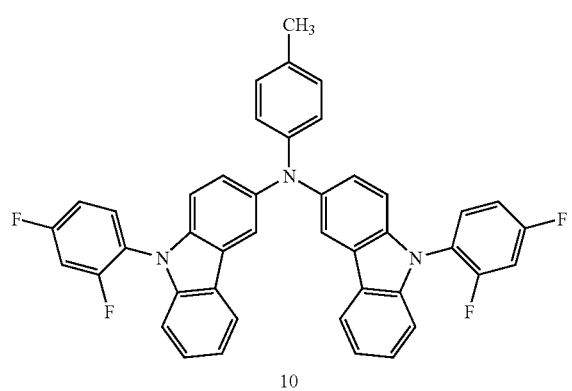
10
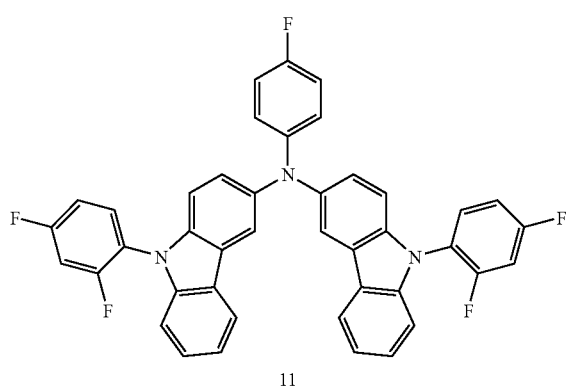
11
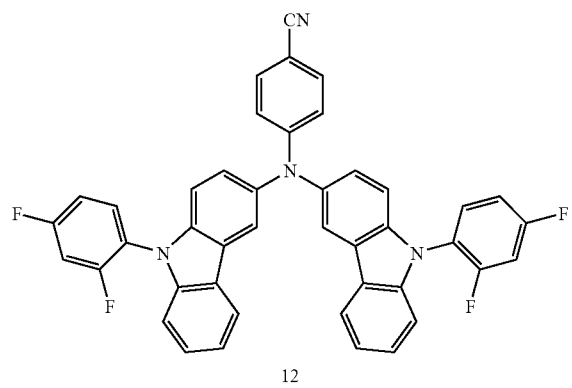
12
-continued
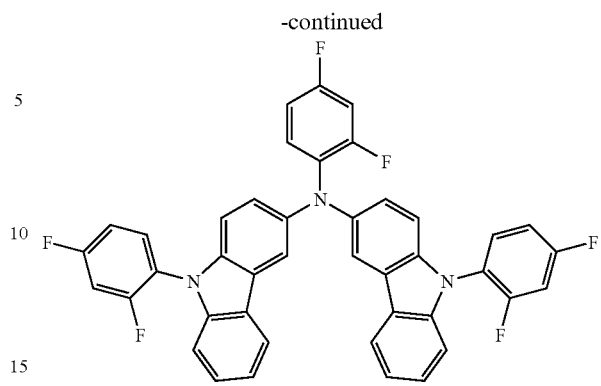
13
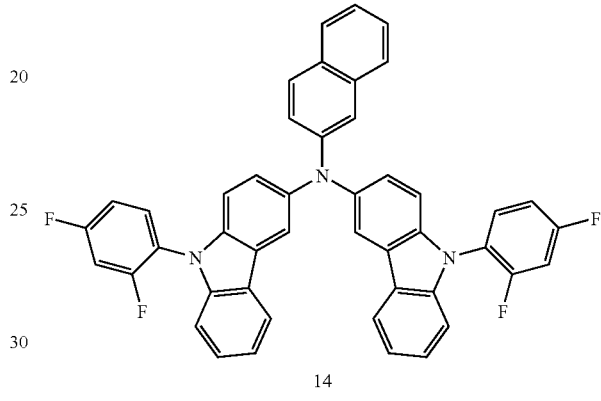
14
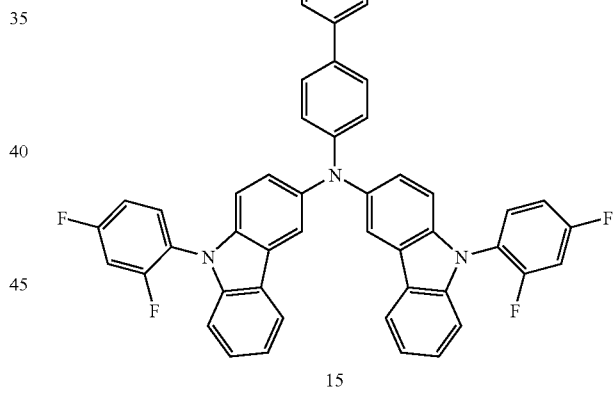
15
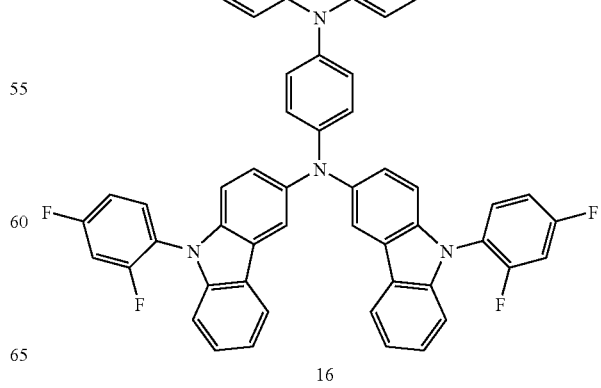
16

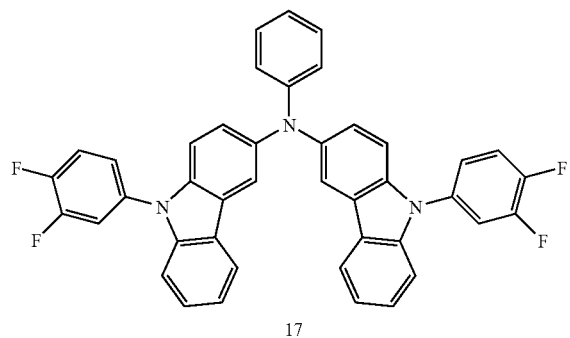
17
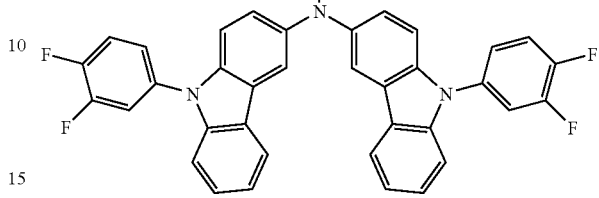
21
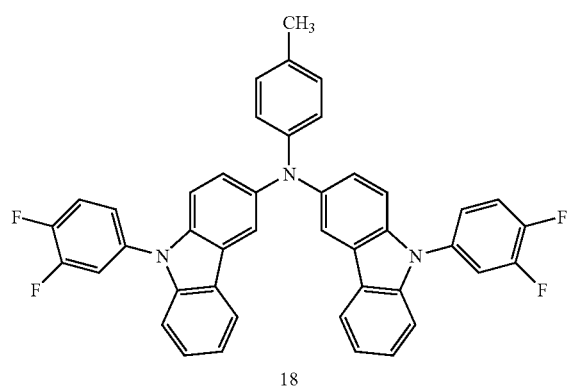
18
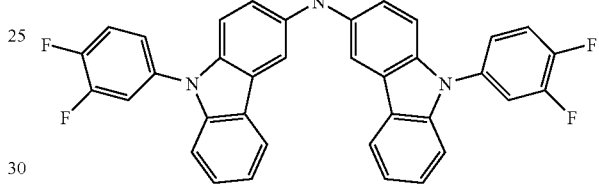
22
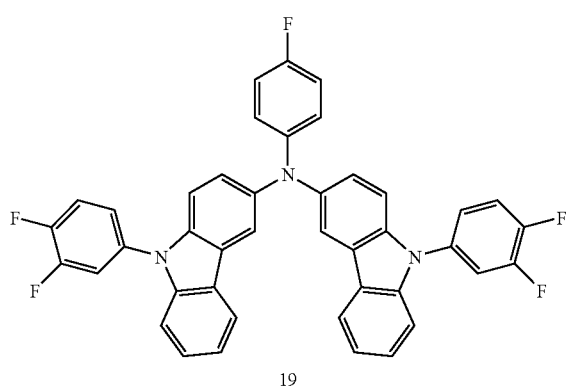
19
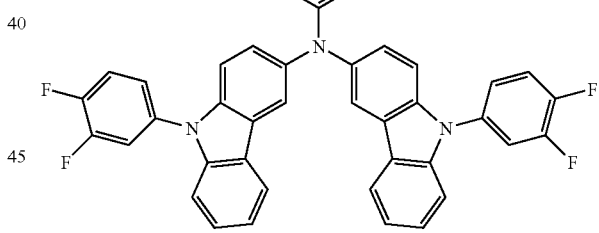
23
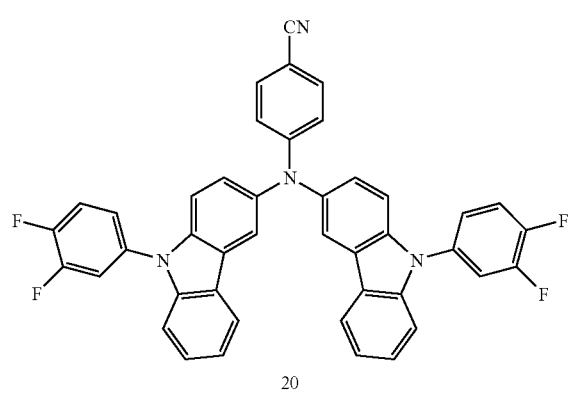
20
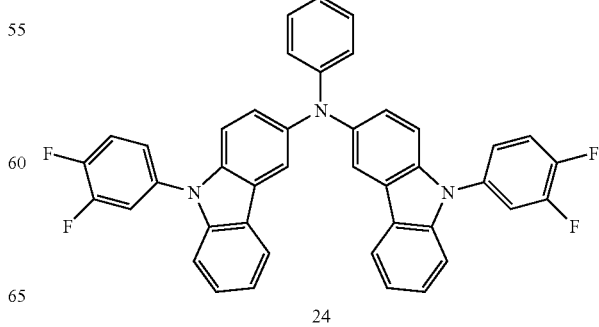
24

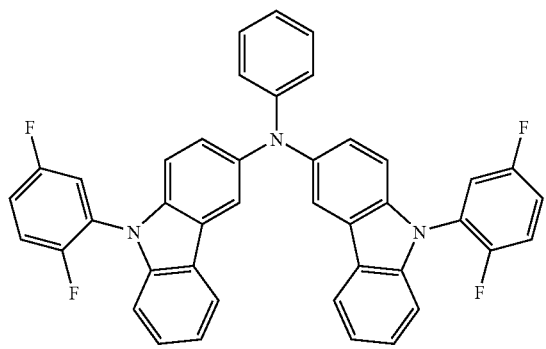
25
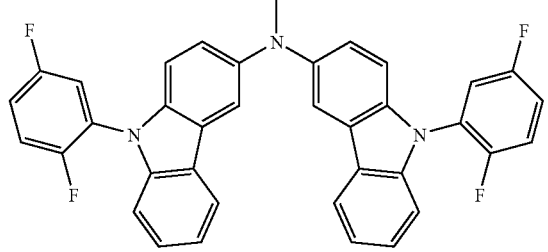
26
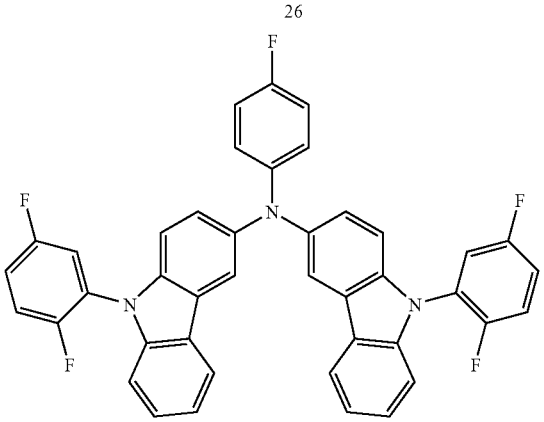
27
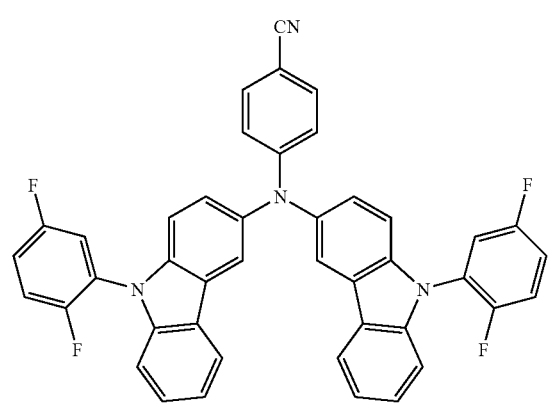
28
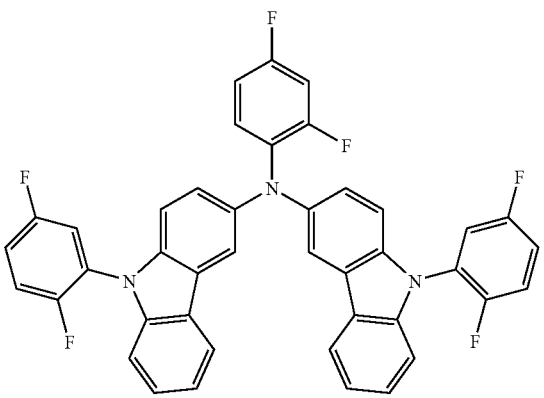
29
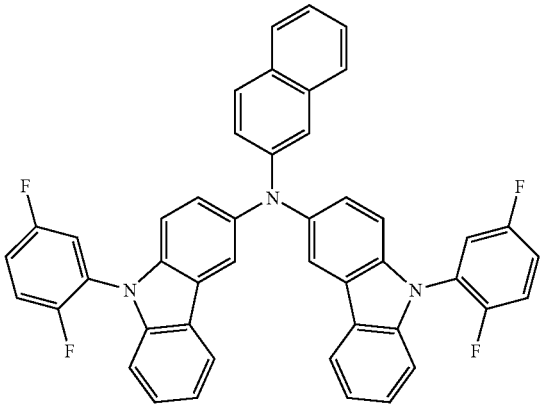
30
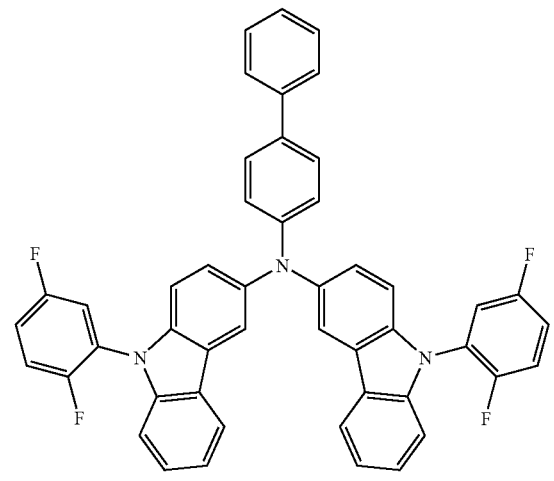
31

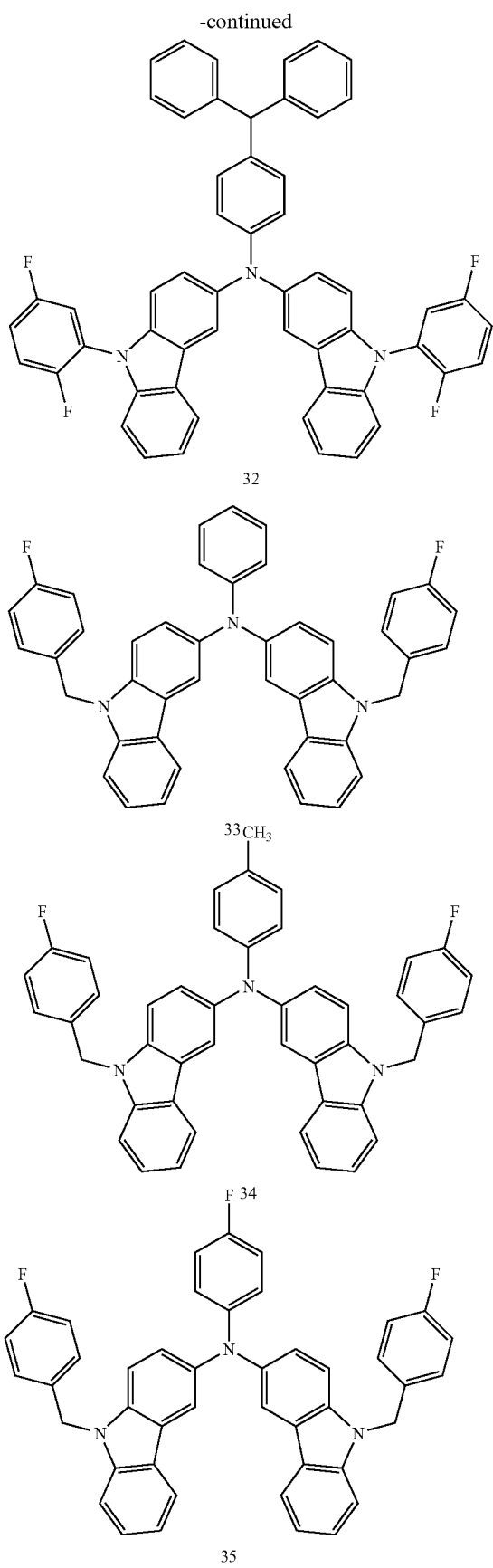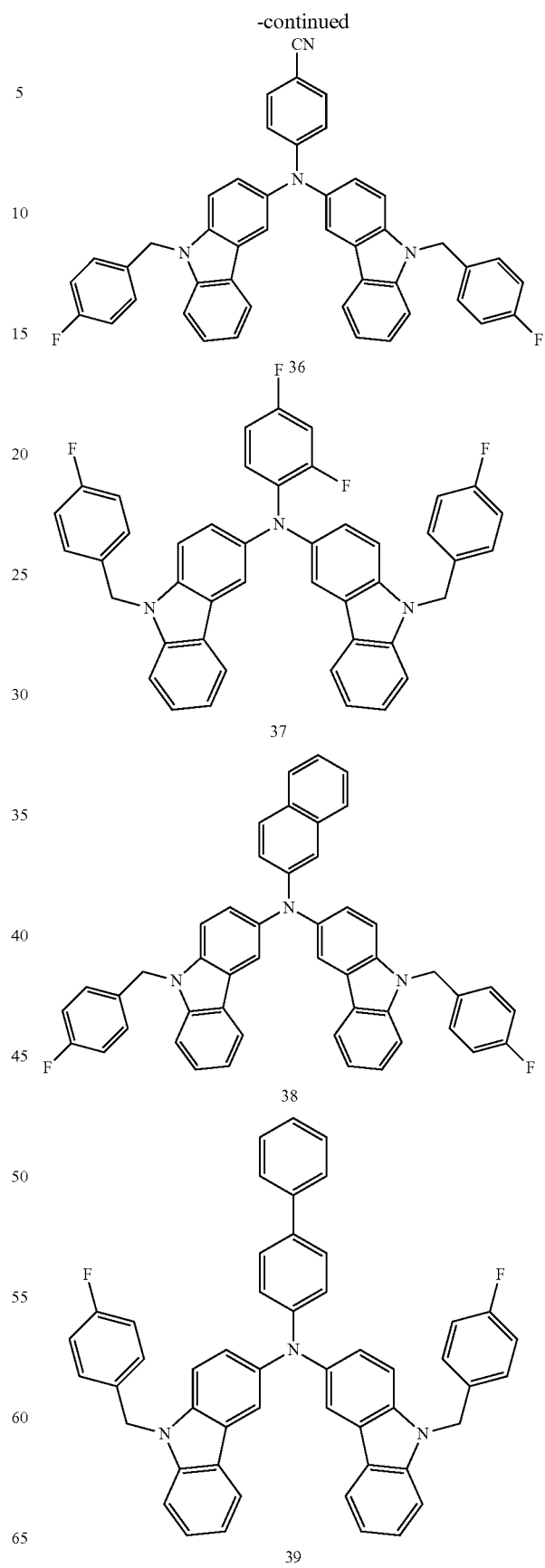

-continued
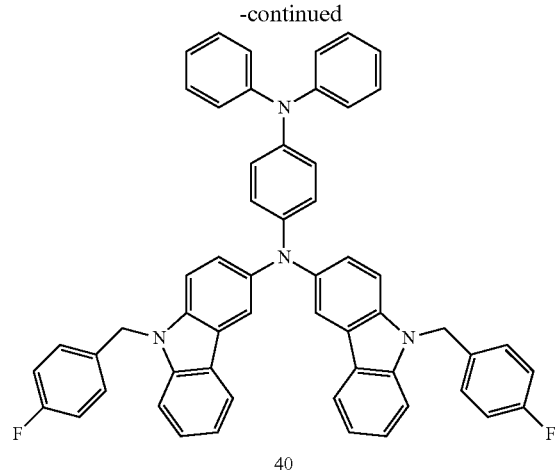
40
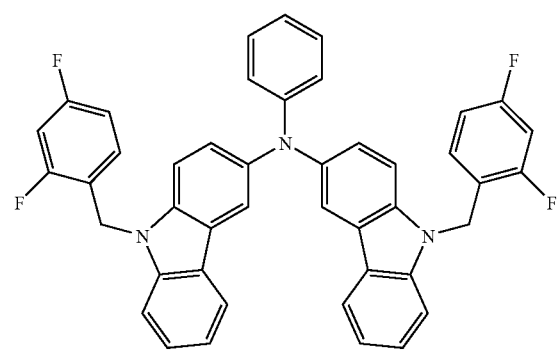
41
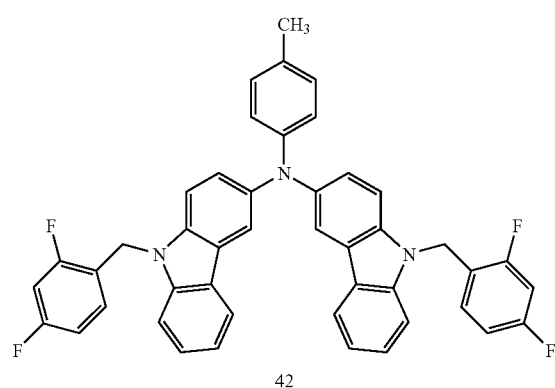
42
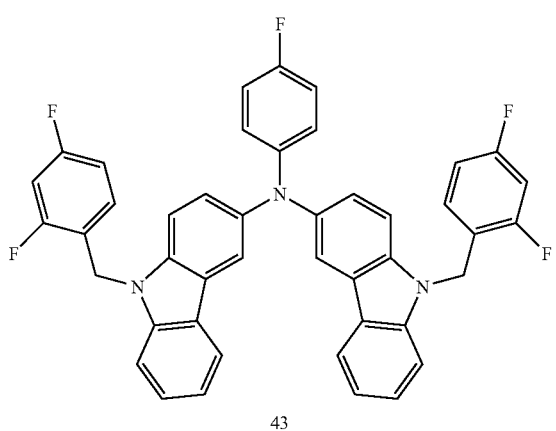
43
-continued
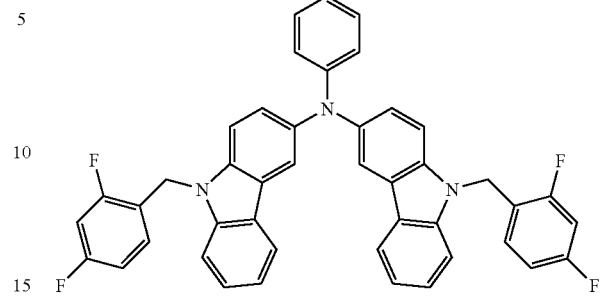
44
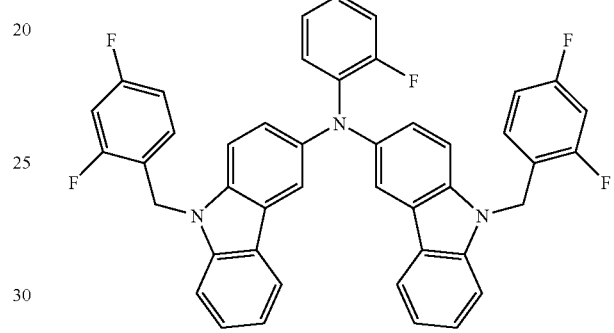
45
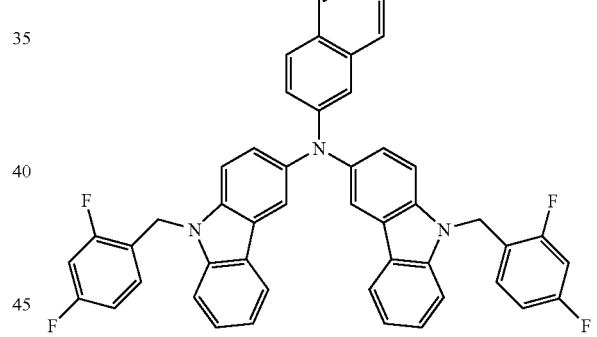
46
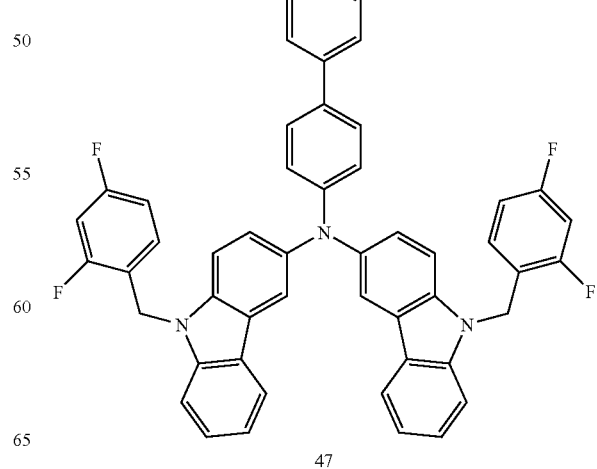
47

-continued
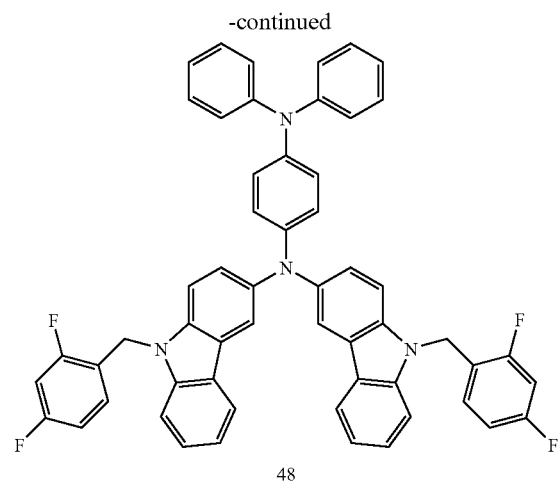
48
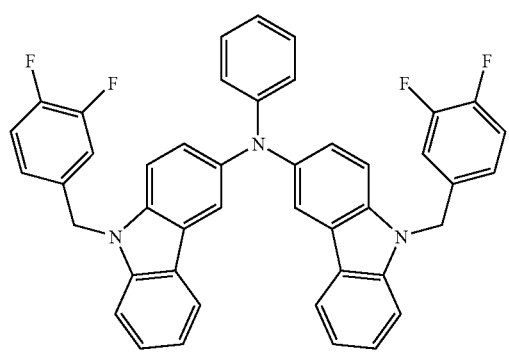
49
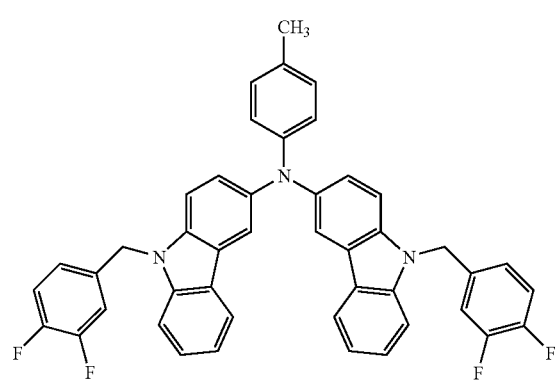
50
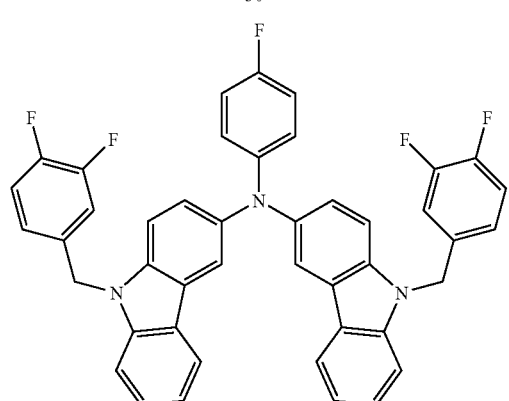
51
-continued
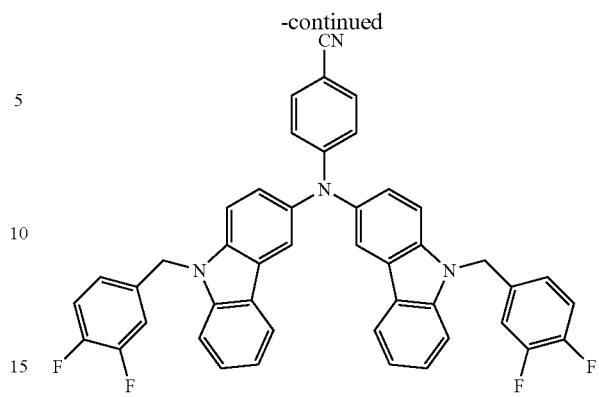
52
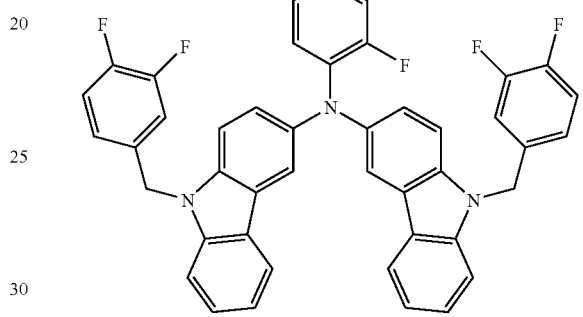
53
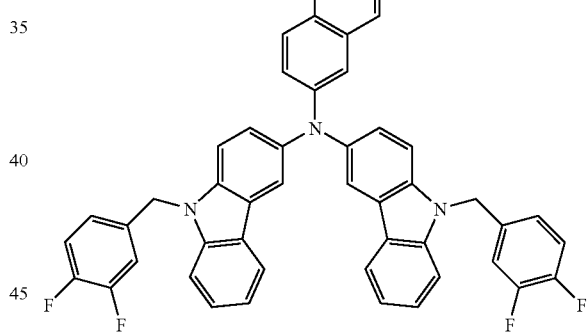
54
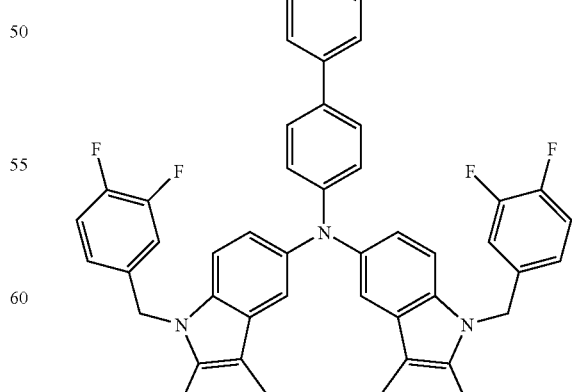
55

-continued

56

57

58

59

-continued

60

61

62

-continued
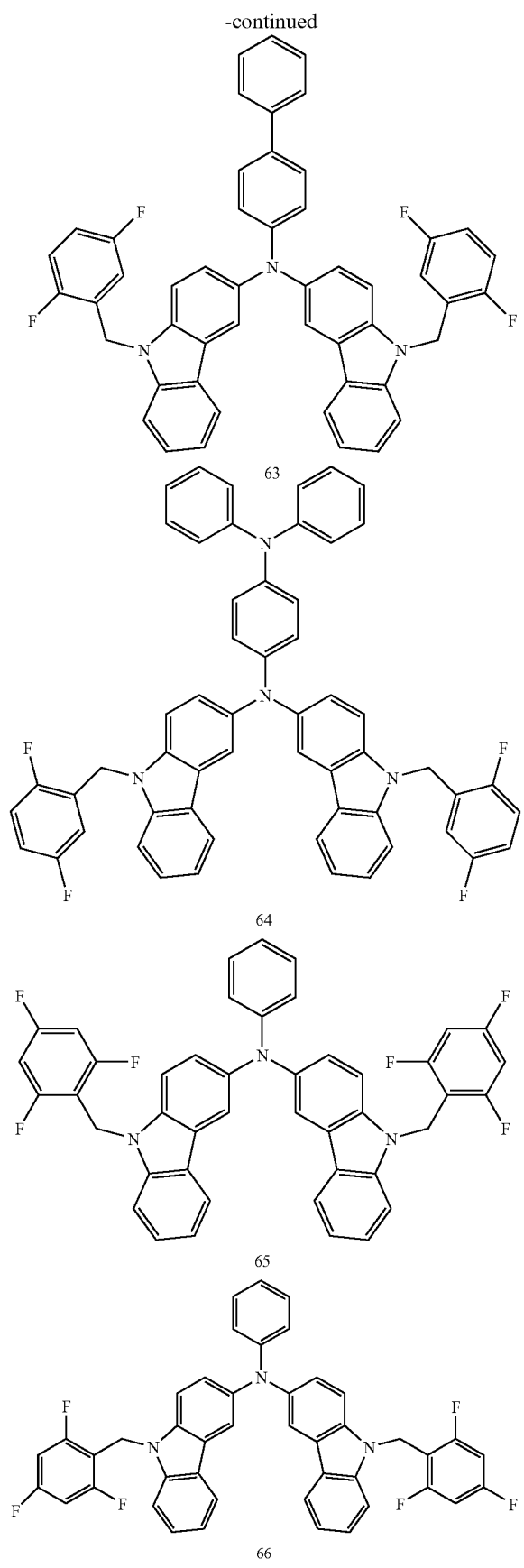
63
64
65
66
-continued
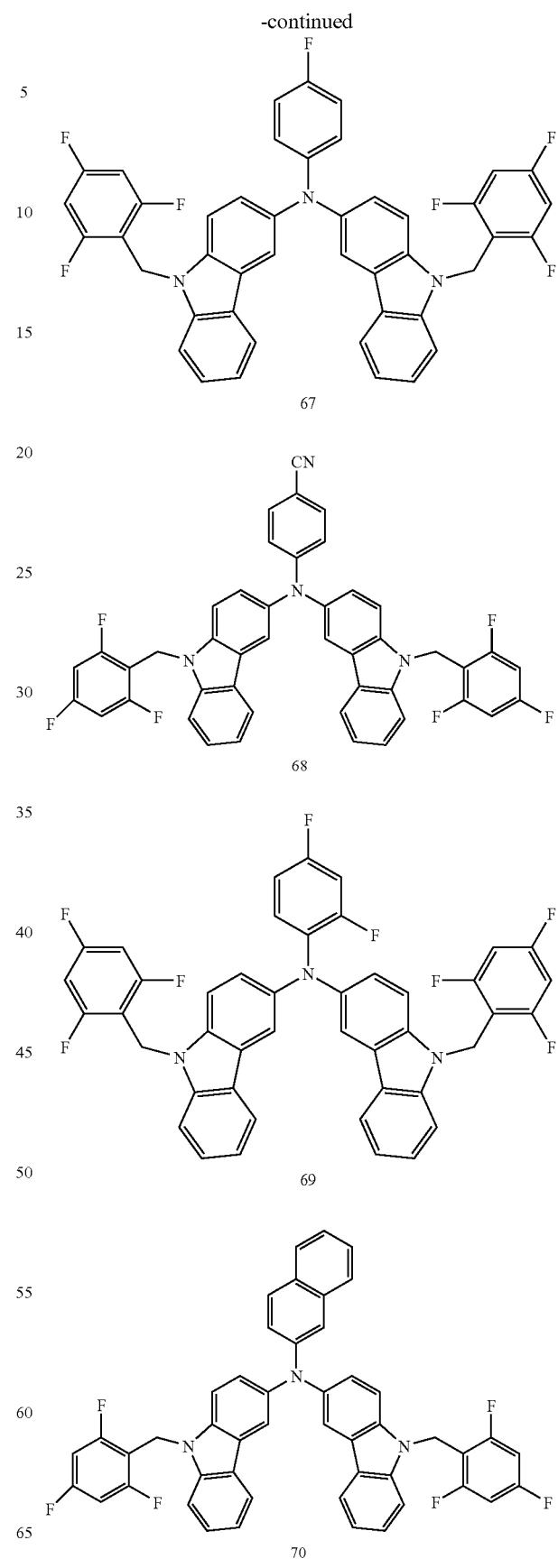
67
68
69
70

-continued
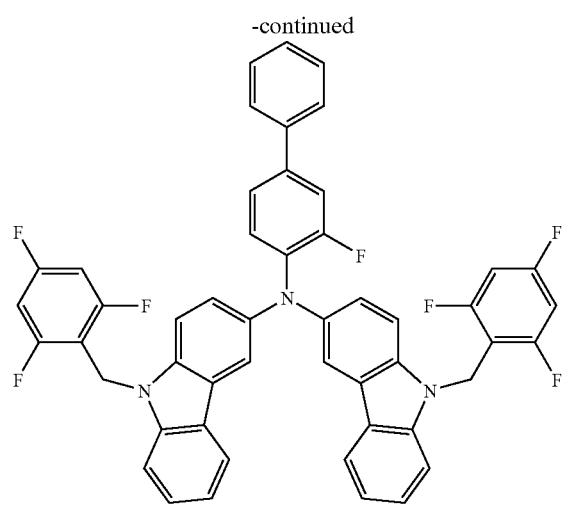
71
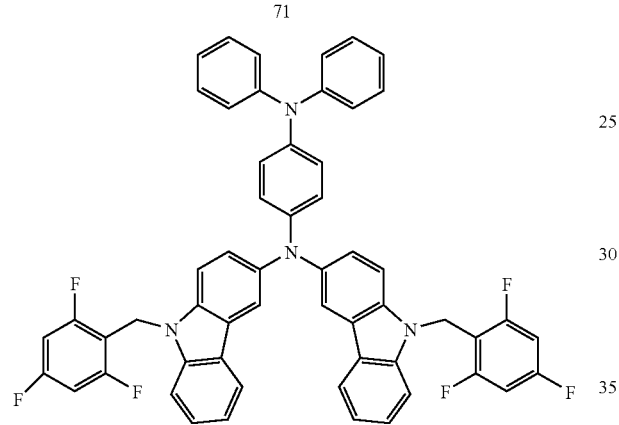
72
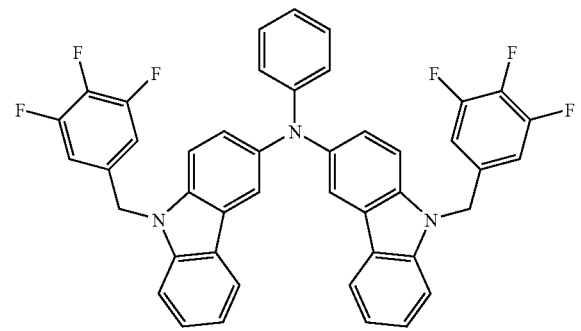
73
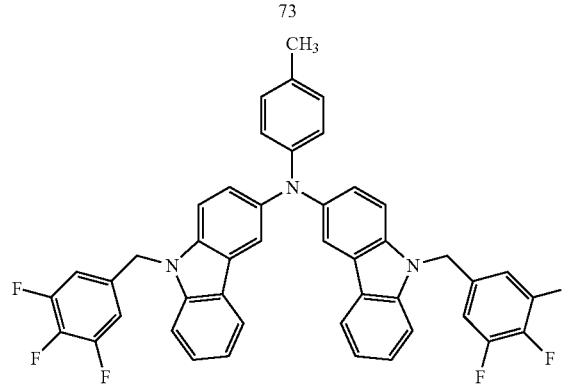
74
-continued
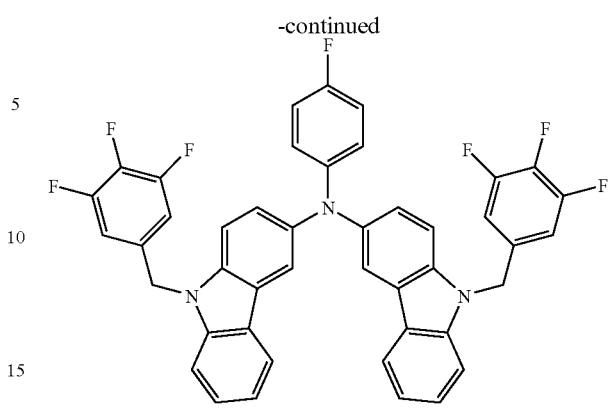
75
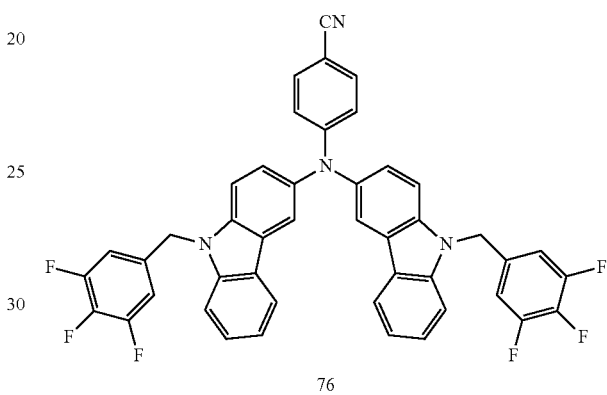
76
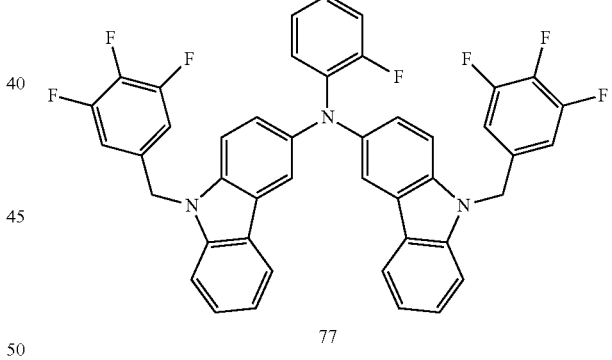
77
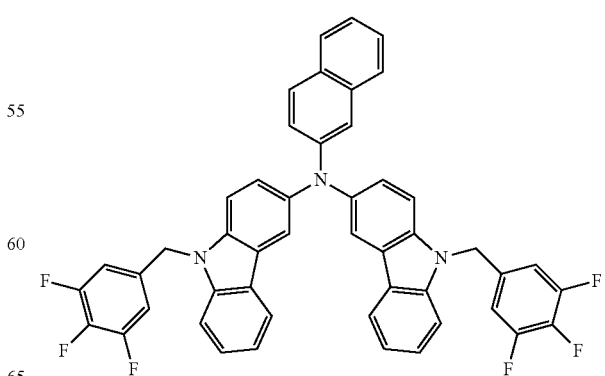
78

-continued
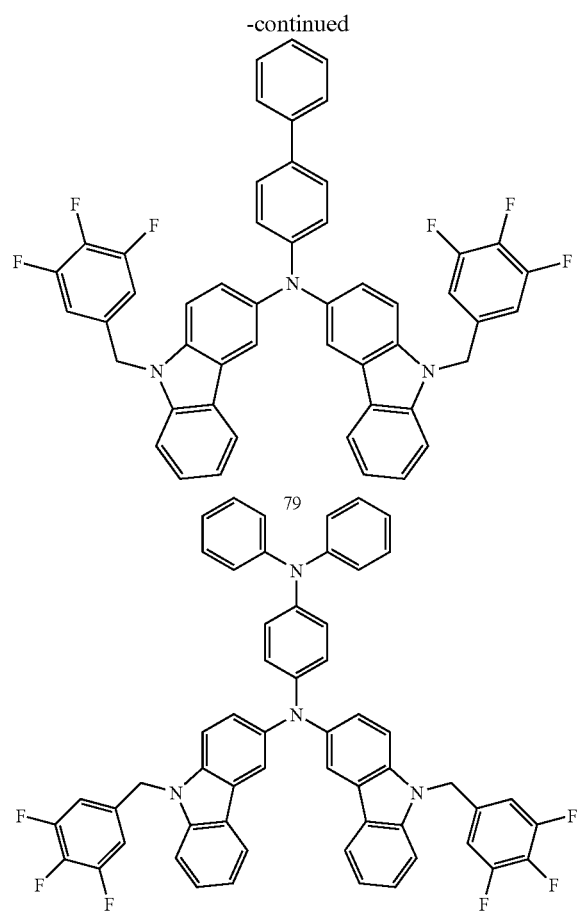
79
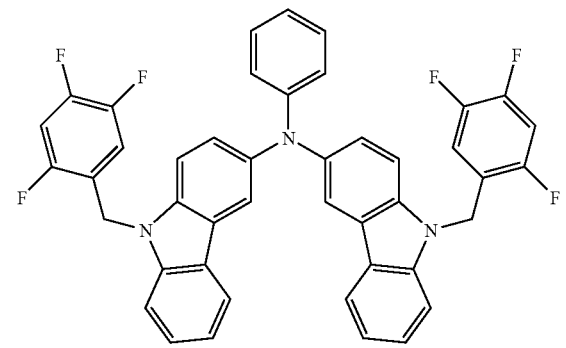
80
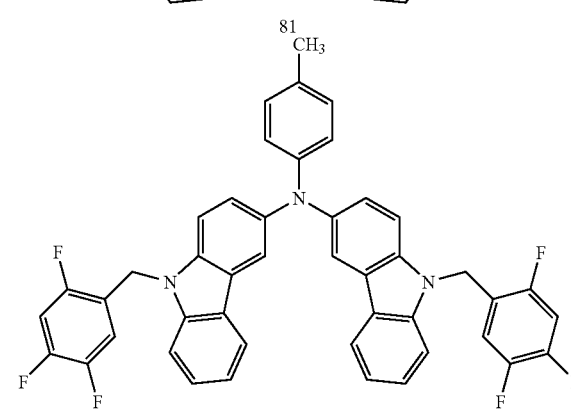
81
82
-continued
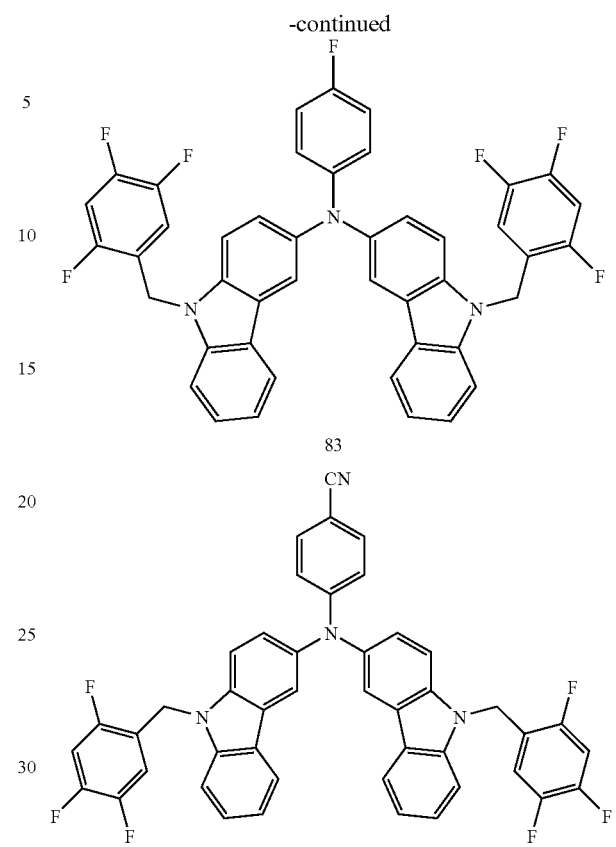
83
84
85
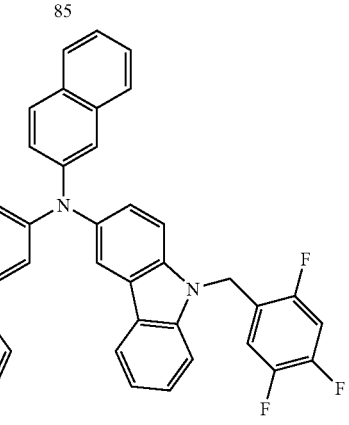
86

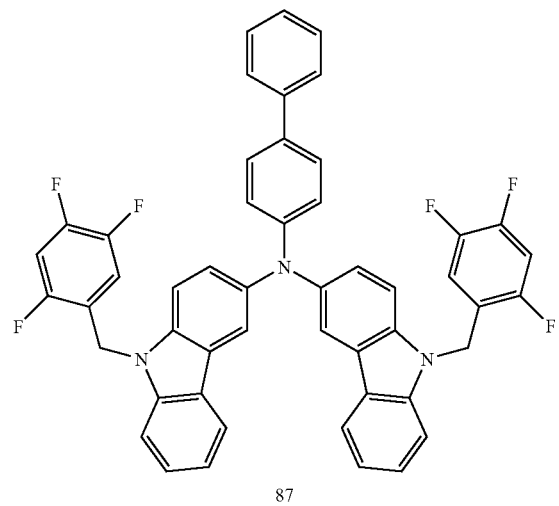
87
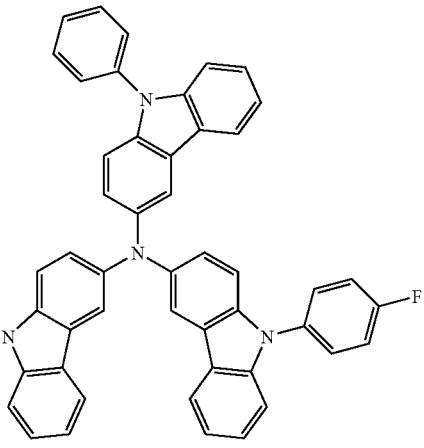
90
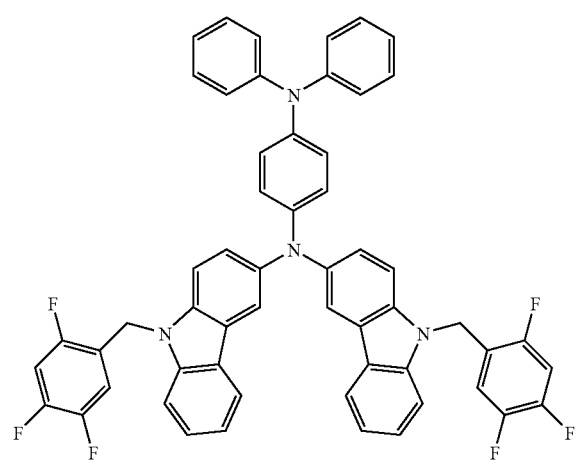
88
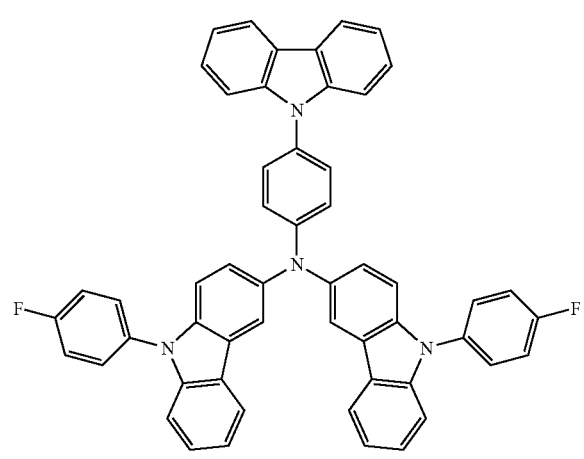
89

-continued

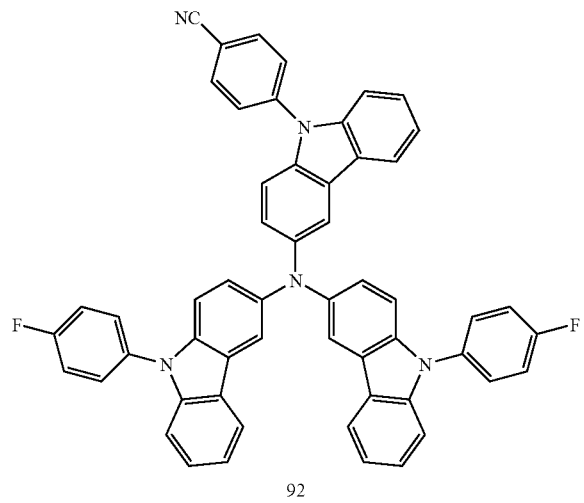

92

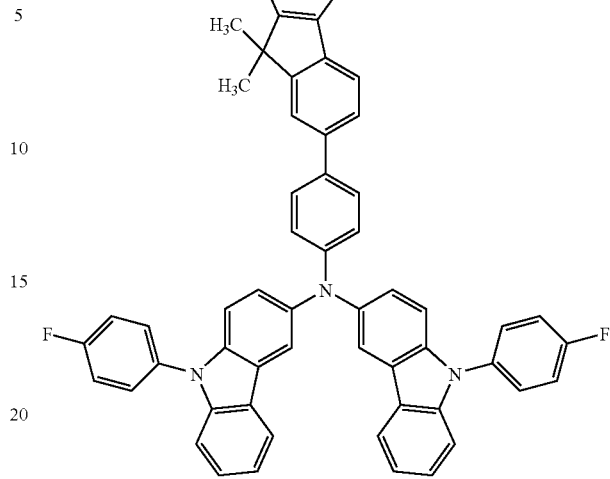

95

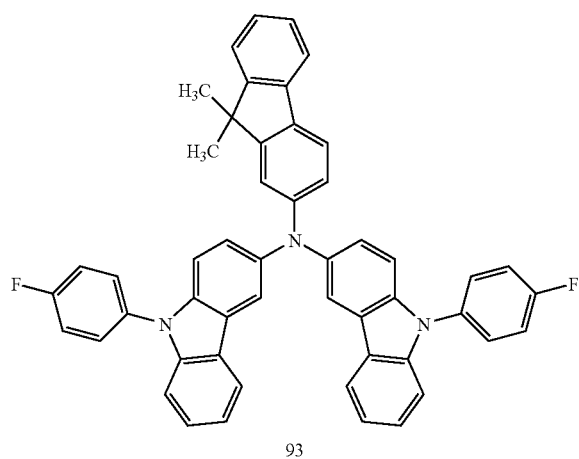

93

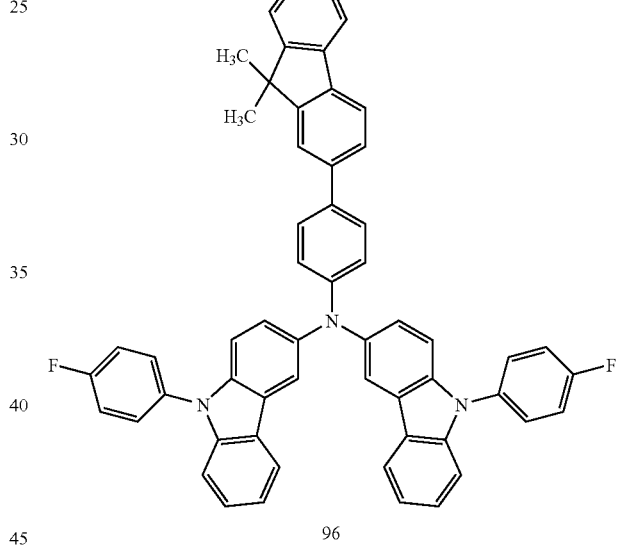

96

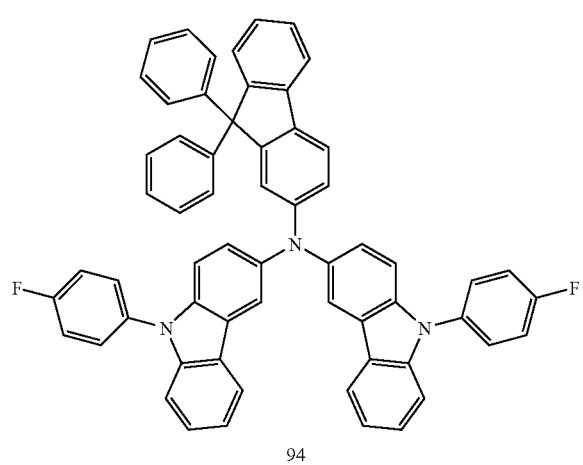

94

A fluorine-containing compound of Formula 1 can be synthesized using various known methods that can be ascertained by persons skilled in the art.

Aspects of the present invention also provide an organic light-emitting device. Examples of organic light-emitting devices are shown in FIGS. 1-7. For example, FIG. 1 shows an organic light-emitting device including: a first electrode; a second electrode; and one or more organic layers interposed between the first electrode and the second electrode, wherein at least one of the one or more organic layers includes a fluorine-containing compound of Formula 1.

The organic light-emitting device can be variously structured. The organic layer including the fluorine-containing compound of Formula 1 may be a hole injection layer, a hole transport layer, or a single layer having hole injection capability and hole transport capability. In addition, the organic light-emitting device may further include one or two intermediate layers. For example, the organic light-emitting device may have one of the following structures:

first electrode/hole injection layer/emitting layer/second electrode (FIG. 2);

first electrode/hole injection and transport layer/emitting layer/electron transport layer/second electrode (FIG. 3);

first electrode/hole injection layer/hole transport layer/ emitting layer/electron transport layer/second electrode (FIG. 4);

first electrode/hole injection layer/hole transport layer/ emitting layer/electron transport layer/electron injection layer/second electrode (FIG. 5); or first electrode/hole injection layer/hole transport layer/ emitting layer/hole blocking layer/electron transport layer/ electron injection layer/second electrode (FIG. 6).

A fluorine-containing compound of Formula 1 is useful as a hole transport material having good hole injection and transport characteristics, in particular as a hole injection material, and can be used as a host material of a blue, green, or red fluorescent or phosphorescent device.

Hereinafter, a method of manufacturing an organic light-emitting device according to an embodiment of the present invention will be described with reference to FIG. 7, which shows an organic light-emitting device that includes an anode, a hole injection layer (HIL), a hole transport layer (HTL), an emitting layer (EML), an electron transport layer (ETL), an electron injection layer (EIL), and a cathode.

First, a first electrode is formed on a substrate by deposition or sputtering using a first electrode material with a high work function. The first electrode may be an anode. Here, the substrate may be a substrate commonly used in organic light-emitting devices. As a non-limiting example, the substrate may be a glass or transparent plastic substrate that is excellent in mechanical strength, thermal stability, transparency, surface smoothness, handling property, and water repellency. The first electrode material may be a transparent material having good conductivity, e.g., indium tin oxide (ITO), indium zinc oxide (IZO), tin oxide ($SnO_2$), or zinc oxide (ZnO).

Next, a hole injection layer (HIL) may be formed on the first electrode using any one of various methods, such as vacuum deposition, spin-coating, casting, or a Langmuir-Blodgett (LB) method.

The hole injection layer material may be a fluorine-containing compound of Formula 1. In addition, the hole injection layer material may be a known hole injection material, e.g., 1,3,5-tricarbazolylbenzene, 4,4'-biscarbazolylbiphenyl, polyvinylcarbazole, m-biscarbazolylphenyl, 4,4'-biscarbazolyl-2,2'-dimethylbiphenyl, 4,4',4''-tri(N-carbazolyl)triphenylamine, 1,3,5-tri(2-carbazolylphenyl)benzene, 1,3,5-tris (2-carbazolyl-5-methoxyphenyl)benzene, bis(4-carbazolylphenyl)silane, N,N'-bis(3-methylphenyl)-N,N'-diphenyl-[1,1-biphenyl]-4,4'-diamine (TPD), N,N'-di (naphthalene-1-yl)-N,N'-diphenyl benzidine (α-NPD), N,N'-diphenyl-N,N'-bis(1-naphthyl)-(1,1'-biphenyl)-4,4'-diamine (NPB), IDE320 (Idemitsu), poly(9,9-dioctylfluorene-co-N-(4-butylphenyl)diphenylamine) (TFB), poly(9,9-dioctylfluorene-co-bis-N,N-(4-butylphenyl-bis-N,N-phenyl-1,4-phenylenediamine) (PFB), etc., but is not limited thereto.

The hole injection layer may be formed using any one of various methods, such as vacuum deposition, spin-coating, casting, or an LB method.

If the hole injection layer is formed using a vacuum deposition process, the deposition conditions vary according to the type of hole injection layer material, the structure and thermal characteristics of the hole injection layer, etc. For example, the hole injection layer may be deposited to a thickness of 10 Å to 5 μm at a deposition rate of 0.01 to 100 Å/sec, at a temperature of 100 to 500° C. and in a vacuum level of $10^{-8}$ to $10^{-3}$ torr.

If the hole injection layer is formed using a spin-coating process, the coating conditions vary according to the type of hole injection layer material, the structure and thermal characteristics of the hole injection layer, etc. For example, the spin-coating may be performed at a coating speed of about 2,000 to 5,000 rpm, and, after the spin-coating, a thermal treatment may be performed at a temperature of about 80 to 200° C. for the purpose of solvent removal.

A hole transport layer may be formed using any one of various methods, such as vacuum deposition, spin-coating, casting, or an LB method. If the hole transport layer is formed using vacuum deposition or spin-coating, the deposition or coating conditions vary according to the type of compound used, but are generally about the same as those used for the formation of the hole injection layer.

The hole transport layer material may be a fluorine-containing compound of Formula 1. In addition or alternatively, the hole transport layer material may be a known material used in hole transport layers, e.g., a carbazole derivative such as N-phenylcarbazole or polyvinylcarbazole; an amine derivative having an aromatic fused ring such as N,N'-bis(3-methylphenyl)-N,N'-diphenyl-[1,1-biphenyl]-4,4'-diamine (TPD) or N,N'-di(naphthalene-1-yl)-N,N'-diphenylbenzidine (α-NPD); etc.

An emitting layer may be formed on the hole injection layer or the hole transport layer according to the color selected for emission. The emitting layer material is not particularly limited, and may be a material selected from known emitting materials and known host/dopant materials. In particular, when using a host material for a blue, green, or red fluorescent or phosphorescent device, a fluorine-containing compound of Formula 1 or other known material may be used as the host material.

A red light-emitting layer may be formed of DCM1, DCM2, Eu(thenoyltrifluoroacetone)3 (Eu(TTA)3), butyl-6-(1,1,7,7,-tetramethyljulolidyl-9-enyl)-4H-pyran (DCJTB), or the like. The red light-emitting layer may also be formed by doping Alq3 with a dopant such as DCJTB, or alternatively, co-depositing Alq3 and rubrene followed by doping with a dopant. The red light-emitting layer may also be formed by doping 4,4'-N—N'-dicarbazole-biphenyl (CBP) with a dopant such as BTPIr or RD 61. As such, the red light-emitting layer can be formed using various modified methods.

A green light-emitting layer may be formed of Coumarin 6, C545T quinacridone, Ir(ppy)$_3$, or the like. In addition or alternatively, the green light-emitting layer may also be formed of a combination of CBP with Ir(ppy)3 as a dopant or a combination of Alq3 as a host with a coumarin-based material as a dopant. As such, the green light-emitting layer may be formed using various materials and methods. Examples of the coumarin-based dopant include C314S, C343S, C7, C7S, C6, C6S, C314T, and C545T.

A blue light-emitting layer may be formed of oxadiazole dimer dyes (Bis-DAPOXP), spiro compounds (Spiro-DPVBi, Spiro-6P), triarylamine compounds, bis(styryl) amine (DPVBi, DSA), Flrpic, CzTT anthracene, TPB, PPCP, DST, TPA, OXD-4, BBOT AZM-Zn, BH-013X (Idemitsu), which is a naphthalene moiety-containing aromatic hydrocarbon compound, or the like. The blue light-emitting layer may also be formed of a combination of IDE140 (trade name, Idemitsu) with a dopant, IDE105 (trade name, Idemitsu). As such, the blue light-emitting layer can be formed using various materials and methods.

The emitting layer may be formed to a thickness of 200 to 500 Å. As a non-limiting example, the emitting layer may be formed to a thickness of 300 to 400 Å. Respective red, green, and blue light-emitting layers of R, G, and B regions may have the same or different thicknesses. If the thickness of the emitting layer is less than 200 Å, a device lifetime may be lowered. On the other hand, if the thickness of the emitting layer exceeds 500 Å, the driving voltage may be significantly increased.

The emitting layer may be formed using any one of various known methods, such as vacuum deposition, spin-coating, casting, or an LB method. When forming the emitting layer using vacuum deposition or spin-coating, the deposition or coating conditions vary according to the type of compound used, but are generally about the same as those used for the formation of the hole injection layer.

A hole blocking layer (not shown) may be selectively formed on the emitting layer by vacuum deposition or spin coating using a hole blocking material. The hole blocking material is not particularly limited, but should have electron transport capability and a higher ionization potential than an emitting compound. For example, the hole blocking material may be bis(2-methyl-8-quinolato)-(p-phenylphenolato)-aluminum (Balq), bathocuproine (BCP), tris(N-aryl benzimidazole) (TPBI), or the like.

The hole blocking layer may be formed to a thickness of 30 to 60 Å. As a non-limiting example, the hole blocking layer may be formed to a thickness of 40 to 50 Å. If the thickness of the hole blocking layer is less than 30 Å, hole blocking characteristics may be lowered. On the other hand, if the thickness of the hole blocking layer exceeds 50 Å, the driving voltage may be increased.

The hole blocking layer may be formed using any one of various known methods, such as vacuum deposition, spin-coating, casting, or an LB method. When forming the hole blocking layer using vacuum deposition or spin-coating, the deposition or coating conditions vary according to the type of compound used, but are generally about the same as those used for the formation of the hole injection layer.

An electron transport layer is selectively formed on the emitting layer or the hole blocking layer by vacuum deposition or spin coating using an electron transport material. The electron transport material is not particularly limited, but may be Alq3, or the like.

The electron transport layer may be formed to a thickness of 100 to 400 Å. As a non-limiting example, the electron transport layer may be formed to a thickness of 250 to 350 Å. If the thickness of the electron transport layer is less than 100 Å, an electron transport rate may be excessively increased, thereby causing charge imbalance. On the other hand, if the thickness of the electron transport layer exceeds 400 Å, the driving voltage may be increased.

The electron transport layer may be formed using any one of various known methods, such as vacuum deposition, spin-coating, casting, or an LB method. When forming the electron transport layer using vacuum deposition or spin-coating, the deposition or coating conditions vary according to the type of compound used, but are generally about the same as those used for the formation of the hole injection layer.

An electron injection layer may be formed on the emitting layer, the hole blocking layer, or the electron transport layer using vacuum deposition or spin coating. The electron injection layer material may be $BaF_2$, LiF, NaCl, CsF, $Li_2O$, BaO, Liq, or the like, but is not limited thereto.

The electron injection layer may be formed to a thickness of 2 to 10 Å. As a non-limiting example, the electron injection layer may be formed to a thickness of 2 to 5 Å. As a specific, non-limiting example, the electron injection layer may be formed to a thickness of 2 to 4 Å. If the thickness of the electron injection layer is less than 2 Å, an electron injection effect may be insufficient. On the other hand, if the thickness of the electron injection layer exceeds 10 Å, the driving voltage may be increased.

The electron injection layer may be formed using any one of various known methods, such as vacuum deposition, spin-coating, casting, or an LB method. When forming the electron injection layer using vacuum deposition or spin-coating, the deposition or coating conditions vary according to the type of compound used, but are generally about the same as those used for the formation of the hole injection layer.

Next, a second electrode material is deposited on the electron injection layer to form a second electrode, thereby completing the manufacture of an organic light-emitting device.

A second electrode material may be a transparent metal oxide with good conductivity, e.g., indium tin oxide (ITO), indium zinc oxide (IZO), tin oxide ($SnO_2$), or zinc oxide (ZnO). In addition, the second electrode may be formed as a thin film using lithium (Li), magnesium (Mg), aluminum (Al), aluminum-lithium (Al—Li), calcium (Ca), magnesium-indium (Mg—In), magnesium-silver (Mg—Ag), calcium (Ca)-aluminum (Al), etc., to be used as a reflective electrode, a translucent electrode, or a transparent electrode. The second electrode material is not limited to the above-exemplified metals or metal-metal combinations.

The first electrode and the second electrode can serve as an anode and a cathode, respectively. Alternatively, the first electrode can be a cathode, and the second electrode can be an anode.

Hereinafter, exemplary synthesis examples of compounds 1, 3, 6, and 33 represented in Formula 3 and working examples will be described. The following examples are for illustrative purposes only and are not intended to limit the scope of the invention.

Synthesis Example 1

Synthesis of Compound 1

Compound 1 was synthesized according to Reaction Scheme 1 below.

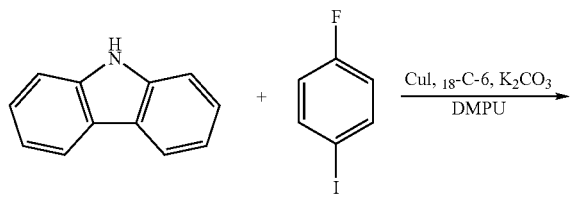

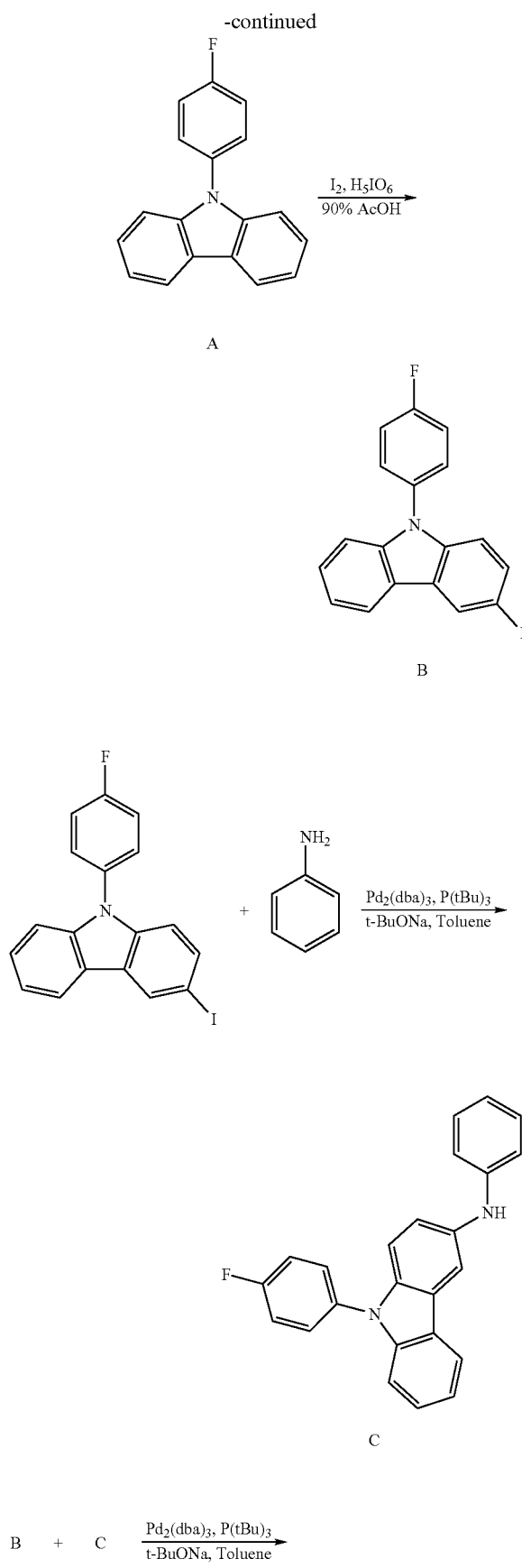

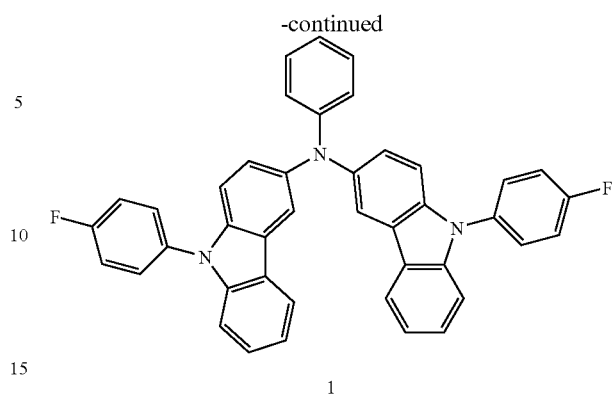

Synthesis of Intermediate A

Carbazole (16.7 g, 100 mmol), 4-fluoro-iodobenzene (28.9 g, 130 mmol), CuI (1.9 g, 10 mmol), $K_2CO_3$ (138 g, 1.0 mol), and 18-crown-6 (530 mg, 2 mmol) were dissolved in 1,3-dimethyl-3,4,5,6-tetrahydro-(1H)-pyrimidinone (DMPU) (500 ml), and the reaction mixture was stirred at 170° C. for 8 hours.

After the reaction was terminated, the reaction solution was cooled to room temperature and a solid material was filtered out. A trace amount of an ammonia solution was added to the filtrate, and the resultant solution was extracted three times with diethylether (300 ml). The collected diethylether layer was washed with excess distilled water, dried over $MgSO_4$, filtered, and dried under a reduced pressure to obtain a crude product. The crude product was purified by silica gel column chromatography to give intermediate A as a white solid (23.5 g, yield: 90%). $^1$H NMR ($CDCl_3$, 400 MHz) δ (ppm) 8.09 (d, 2H), 7.56-7.52 (m, 2H), 7.34 (d, 4H), 7.26-7.20 (m, 2H), 7.08-7.03 (m, 2H); $^{13}$C NMR ($CDCl_3$, 100 MHz) δ (ppm) 161.9, 155.4, 139.5, 136.8, 136.7, 126.2, 125.5, 125.3, 123.0, 123.4, 119.9, 113.8, 113.1, 109.6.

Synthesis of Intermediate B

Intermediate A (2.61 g, 10 mmol) was added to 80% acetic acid (100 ml), and iodine (12) (1.357 g, 5.35 mmol) and ortho-periodinic acid ($H_5IO_6$) (0.333 g, 1.46 mmol) in a solid phase were added thereto. The reaction mixture was stirred at 80° C. under a nitrogen atmosphere for two hours.

After the reaction was terminated, the reaction solution was cooled to room temperature, and water was added thereto. The resultant solution was extracted three times with ethylether (50 ml). The collected organic layer was washed with an $NaHCO_3$ solution (30 ml) and brine (50 ml) in sequence, dried over $MgSO_4$, filtered, and dried under a reduced pressure to obtain a crude product. The crude product was purified by silica gel column chromatography to give intermediate B as a white solid (3.37 g, yield: 87%). $^1$H NMR ($CDCl_3$, 400 MHz) δ (ppm) 8.29 (d, 1H), 8.15-8.09 (m, 1H), 7.74 (d, 1H), 7.56-7.52 (m, 4H), 7.37-7.29 (m, 2H), 7.08-7.03 (m, 2H); $^{13}$C NMR ($CDCl_3$, 100 MHz) δ (ppm) 161.9, 155.4, 139.5, 138.1, 135.9, 135.8, 130.7, 126.5, 125.5, 125.3, 124.4, 128.1, 118.3, 117.9, 117.2, 113.8, 113.1, 108.7.

Synthesis of Intermediate C

Intermediate B (3.87 g, 10 mmol) and aniline (1 g, 11 mmol) were dissolved in toluene (50 ml), and t-BuONa (1.44 g, 15 mmol), Pd(dba)$_2$ (0.18 g, 0.2 mmol), and (t-Bu)$_3$P (0.04-0.06 g, 0.2-0.3 mmol) were added thereto. The reaction mixture was stirred at 80° C. for five hours. The reaction solution was extracted three times with ethylether (50 ml). The collected organic layer was dried over magnesium sulfate to evaporate the solvent, and the residue was purified by silica gel column chromatography to give intermediate C (2.5 g, yield: 71%). $^1$H NMR (CDCl$_3$, 400 MHz) δ(ppm) 8.03-7.98 (m, 1H), 7.66 (d, 1H), 7.54 (d, 2H), 7.43 (d, 1H), 7.35-7.33 (m, 3H), 7.21-7.15 (m, 2H), 7.07-7.01 (m, 4H), 6.95 (dd, 1H), 6.73 (dt, 1H), 5.68 (s, 1H); $^{13}$C NMR (CDCl$_3$, 100 MHz) δ (ppm) 161.9, 155.5, 144.7, 138.9, 136.6, 136.5, 134.7, 129.4, 128.1, 126.3, 125.5, 125.3, 119.1, 119.0, 118.7, 118.5, 116.8, 113.8, 113.1, 111.2, 109.4, 102.5.

Synthesis of Compound 1

Intermediate C (4.26 g, 11 mmol) and intermediate B (3.52 g, 10 mmol) were dissolved in toluene (50 ml), and t-BuONa (1.44 g, 15 mmol), Pd(dba)$_2$ (0.18 g, 0.2 mmol), and (t-Bu)$_3$P (0.04~0.06 g, 0.2~0.3 mmol) were added thereto. The reaction mixture was stirred at 90° C. for six hours. The reaction solution was extracted three times with ethylether (50 ml). The collected organic layer was dried over magnesium sulfate to evaporate the solvent, and the residue was purified by silica gel column chromatography to give compound 1 (3.91 g, yield: 64%). The structure of compound 1 was determined by $^1$H-NMR and $^{13}$C NMR: $^1$H NMR (CDCl$_3$, 400 MHz) δ (ppm) 7.93 (d, 2H), 7.56-7.44 (m, 14H), 7.37-7.28 (m, 4H), 7.09-7.02 (m, 4H), 6.64-6.59 (m, 1H), 5.69-5.66 (m, 2H); $^{13}$C NMR (CDCl$_3$, 100 MHz) δ (ppm) 161.9, 155.4, 149.7, 143.9, 136.9, 136.7, 135.5, 135.4, 129.4, 126.3, 125.5, 125.3, 122.9, 122.8, 120.4, 118.0, 116.7, 116.4, 114.4, 113.8, 113.1, 110.9, 108.4.

Synthesis Example 2

Synthesis of Compound 3

Compound 3 was synthesized according to Reaction Scheme 2 below.

<Reaction Scheme 2>

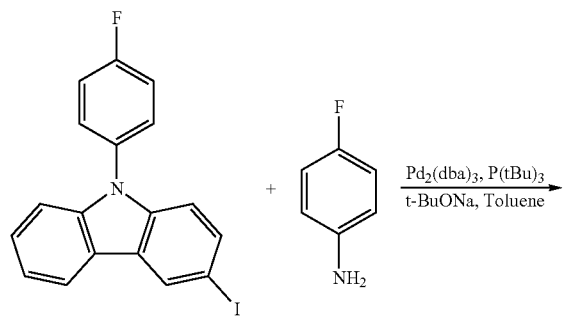

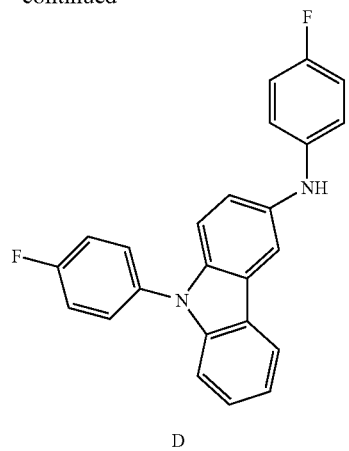

D

B + D $\xrightarrow{\text{Pd}_2(\text{dba})_3, \text{P(tBu)}_3}{\text{t-BuONa, Toluene}}$

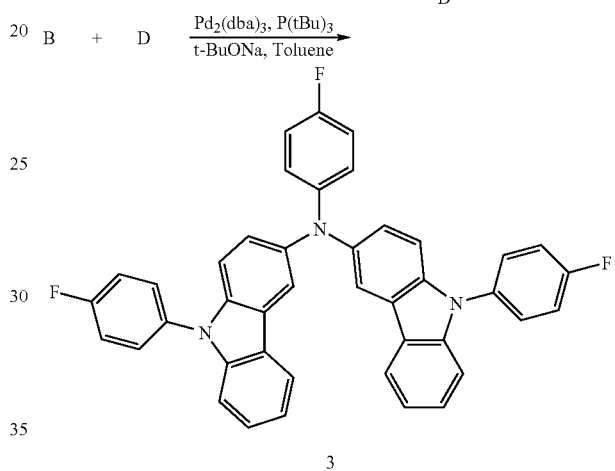

3

Synthesis of Intermediate D

Intermediate B (see reaction scheme 1) (3.87 g, 10 mmol) and 4-fluoroaniline (1.4 g, 11 mmol) were dissolved in toluene (50 ml), and t-BuONa (1.44 g, 15 mmol), Pd(dba)$_2$ (0.18 g, 0.2 mmol), and (t-Bu)$_3$P (0.04~0.06 g, 0.2~0.3 mmol) were added thereto. The reaction mixture was stirred at 80° C. for five hours. The reaction solution was extracted three times with ethylether (20 ml). The collected organic layer was dried over magnesium sulfate to evaporate the solvent, and the residue was purified by silica gel column chromatography to give intermediate D (2.9 g, yield: 78%). $^1$H NMR (CDCl$_3$, 400 MHz) δ (ppm) 8.04-8.00 (m, 1H), 7.96-7.92 (m, 2H), 7.66 (d, 1H), 7.56-7.52 (m, 2H), 7.43 (d, 1H), 7.35-7.32 (m, 4H), 7.23-7.18 (m, 2H), 7.08-6.96 (m, 2H), 6.95 (dd, 1H), 5.79 (s, 1H); $^{13}$C NMR (CDCl$_3$, 100 MHz) δ (ppm) 162.0, 161.0, 155.5, 154.5, 140.8, 140.7, 138.9, 136.6, 136.5, 134.7, 127.1, 126.3, 125.5, 125.3, 119.1, 119.1, 118.7, 118.5, 116.5, 115.8, 113.8, 113.1, 111.7, 111.5, 111.2, 109.4, 102.5.

Synthesis of Compound 3

Intermediate D (3.7 g, 10 mmol) and intermediate B (4.3 g, 11 mmol) were dissolved in toluene (50 ml), and t-BuONa (1.44 g, 15 mmol), Pd(dba)$_2$ (0.18 g, 0.2 mmol), and (t-Bu)$_3$P (0.04~0.06 g, 0.2~0.3 mmol) were added thereto. The reaction mixture was stirred at 90° C. for six hours. The reaction solution was extracted three times with ethylether (50 ml).

The collected organic layer was dried over magnesium sulfate to evaporate a solvent, and the residue was purified by silica gel column chromatography to give compound 3 (4.2 g, yield: 67%). The structure of compound 3 was determined by $^1$H-NMR and $^{13}$C NMR: $^1$H NMR (CDCl$_3$, 400 MHz) δ (ppm) 7.93 (d, 2H), 7.56-7.45 (m, 14H), 7.34 (dt, 2H), 7.11-7.02 (m, 6H), 6.78-6.74 (m, 2H); $^{13}$C NMR (CDCl$_3$, 100 MHz) δ (ppm) 162.0, 155.5, 145.7, 145.6, 143.0, 136.9, 136.7, 135.5, 135.5, 126.2, 125.4, 125.2, 125.1, 125.0, 120.4, 120.4, 118.1, 116.7, 116.3, 116.2, 115.5, 114.4, 113.8, 113.1, 110.9, 108.4.

Synthesis Example 3

Synthesis of Compound 6

Compound 6 was synthesized according to Reaction Scheme 3 below.

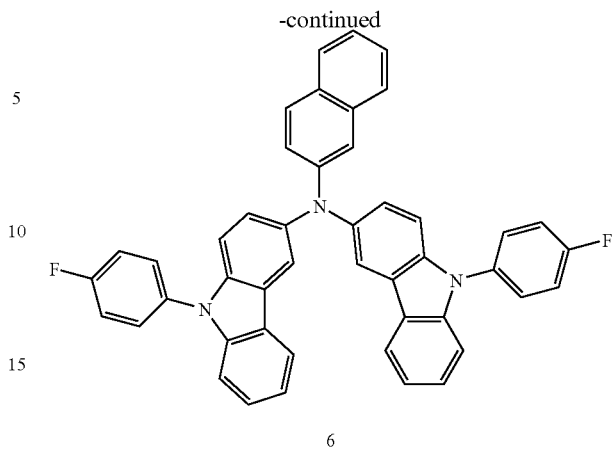

6

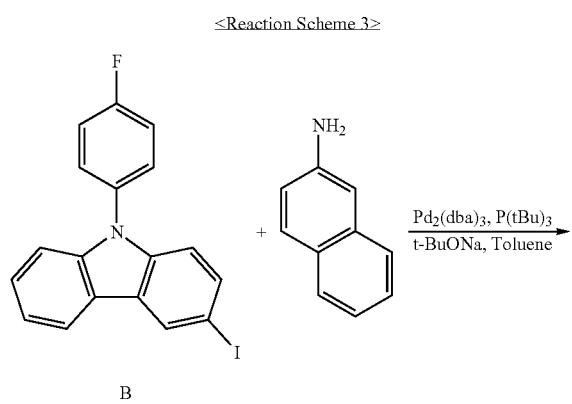

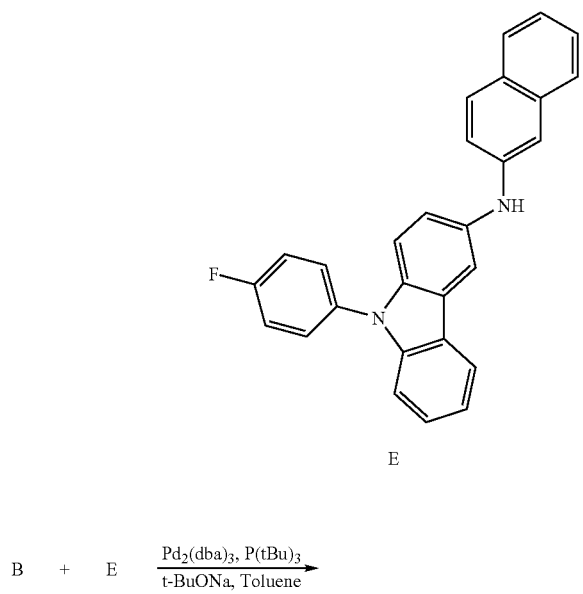

Synthesis of Intermediate E

Intermediate B (3.87 g, 10 mmol) and 2-aminonaphthalene (1.57 g, 11 mmol) were dissolved in toluene (50 ml), and t-BuONa (1.44 g, 15 mmol), Pd(dba)$_2$ (0.18 g, 0.2 mmol), and (t-Bu)$_3$P (0.04~0.06 g, 0.2~0.3 mmol) were added thereto. The reaction mixture was stirred at 80° C. for five hours. The reaction solution was extracted three times with ethylether (50 ml). The collected organic layer was dried over magnesium sulfate to evaporate the solvent, and the residue was purified by silica gel column chromatography to give intermediate E (2.73 g, yield: 68%). $^1$H NMR (CDCl$_3$, 400 MHz) δ (ppm) 8.04-7.99 (d, 1H), 7.79 (d, 1H), 7.67-7.62 (m, 2H), 7.56-7.49 (m, 4H), 7.46-7.41 (m, 2H), 7.36-7.31 (m, 2H), 7.20 (dd, 1H), 7.08-7.03 (m, 2H), 6.95 (dd, 1H), 6.75 (s, 1H); $^{13}$C NMR (CDCl$_3$, 100 MHz) δ (ppm) 161.9, 155.6, 142.1, 138.9, 136.6, 136.5, 135.2, 134.7, 130.2, 130.1, 128.8, 128.7, 127.5, 126.3, 125.5, 125.3, 123.5, 120.4, 119.4, 119.1, 119.0, 118.7, 118.5, 113.8, 113.1, 113.0, 109.4, 104.3.

Synthesis of Compound 6

Intermediate E (4.02 g, 10 mmol) and intermediate B (4.25 g, 11 mmol) were dissolved in toluene (50 ml), and t-BuONa (1.44 g, 15 mmol), Pd(dba)$_2$ (0.18 g, 0.2 mmol), and (t-Bu)$_3$P (0.04~0.06 g, 0.2~0.3 mmol) were added thereto. The reaction mixture was stirred at 90° C. for six hours. The reaction solution was extracted three times with ethylether (50 ml). The collected organic layer was dried over magnesium sulfate to evaporate a solvent, and the residue was purified by silica gel column chromatography to give compound 6 (4.63 g, yield: 70%). The structure of compound 6 was determined by $^1$H-NMR and $^{13}$C NMR: $^1$H NMR (CDCl$_3$, 400 MHz) δ (ppm) 7.93 (d, 2H), 7.87 (d, 2H), 7.71-7.63 (m, 4H), 7.56-7.43 (m, 11H), 7.36-7.32 (m, 4H), 7.11 (dd, 2H), 7.09-7.02 (m, 4H); $^{13}$C NMR (CDCl$_3$, 100 MHz) δ (ppm) 162.5, 156.4, 147.1, 144.2, 136.9, 136.7, 136.5, 136.4, 130.6, 130.2, 129.5, 128.2, 127.6, 126.7, 126.2, 125.5, 125.3, 122.5, 120.4, 120.4, 118.2, 118.1, 116.7, 116.2, 114.4, 113.8, 113.2, 112.8, 108.4, 104.8.

Synthesis Example 4

Synthesis of Compound 33

Compound 33 was synthesized according to Reaction Scheme 4 below.

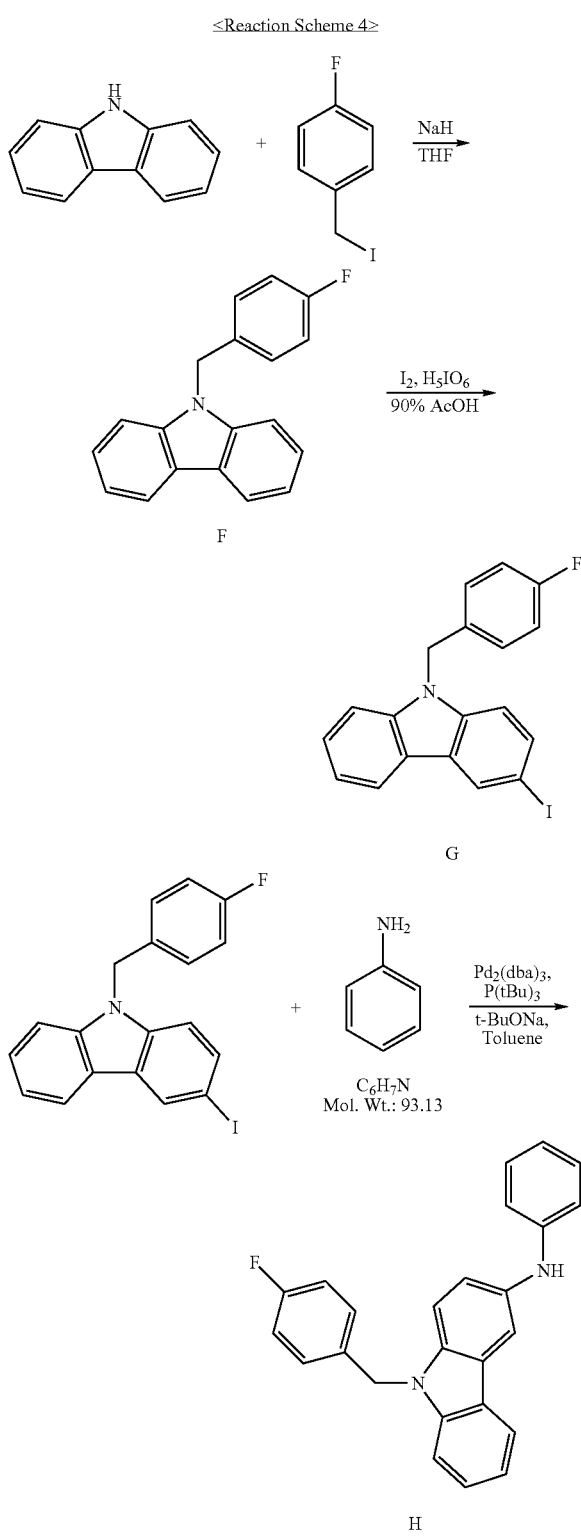

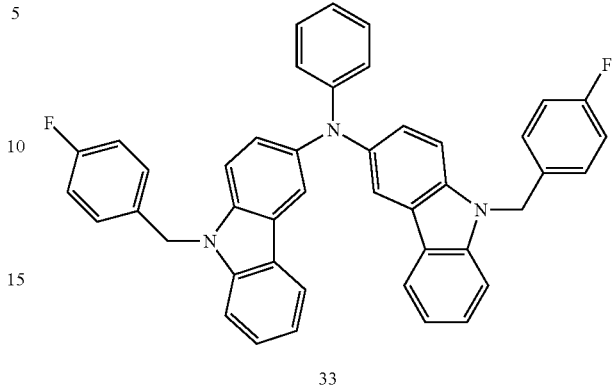

Synthesis of Intermediate F

Carbazole (5.02 g, 30.0 mmol), 4-fluorobenzyl bromide (6.80 g, 36.0 mmol), and 60% NaH (1.44 g, 36.0 mmol) were dissolved in THF (100 ml), and the reaction mixture was stirred at 70° C. under a nitrogen atmosphere for 12 hours. After the reaction was terminated, the reaction solution was cooled to room temperature, distilled water was added thereto, and the resultant solution was extracted three times with diethylether (50 ml). The collected organic layer was dried over magnesium sulfate to evaporate a solvent, and the residue was purified by silica gel column chromatography (10% MC in hexane) to give intermediate F (7.50 g, yield: 91%). $^1$H NMR (CDCl$_3$, 400 MHz) δ (ppm) 7.96 (d, 2H), 7.76, (d, 2H), 7.48-7.44 (dt, 2H), 7.21-7.15 (dt, 2H), 7.09-7.03 (m, 4H), 5.79 (s, 2H); $^{13}$C NMR (CDCl$_3$, 100 MHz) δ (ppm) 164.8, 158.3, 140.2, 134.2, 134.1, 129.0, 128.8, 126.1, 122.5, 120.5, 119.3, 115.9, 115.2, 109.7, 45.0.

Synthesis of Intermediate G

Intermediate F (7.23 g, 26.3 mmol) was added to 80% acetic acid (100 ml), and iodine (12) (3.70 g, 0.55 equiv.) and ortho-periodinic acid (H$_5$IO$_6$) (900 mg, 0.15 equiv.) in a solid phase were added thereto. The reaction mixture was stirred at 80° C. under a nitrogen atmosphere for two hours.

After the reaction was terminated, the reaction solution was cooled to room temperature, water was added thereto, and the resultant solution was extracted three times with ethylether (50 ml). The collected organic layer was washed with an NaHCO$_3$ solution (30 ml) and brine (50 ml) in sequence, dried over MgSO$_4$, filtered, and dried under a reduced pressure to obtain a crude product. The crude product was purified by silica gel column chromatography (10% MC in hexane) to give intermediate G as a white solid (9.07 g, yield: 86%). $^1$H NMR (CDCl$_3$, 400 MHz) δ (ppm) 8.40 (s, 1H), 8.04 (d, 1H), 7.64 (d, 1H), 7.44-7.32 (m, 1H), 7.44-7.24 (m, 2H), 7.10-7.03 (m, 3H), 6.92 (t, 2H); $^{13}$C NMR (CDCl$_3$, 100 MHz) δ (ppm) 163.3, 160.9, 140.4, 139.5, 134.8, 134.0, 129.4, 129.2, 127.9 (d), 126.6, 120.6, 119.8, 115.7 (d), 110.8, 108.9, 81.8, 45.9.

Synthesis of Intermediate H

Intermediate G (4.01 g, 10 mmol) and aniline (1.11 g, 12 mmol) were dissolved in toluene (50 ml), and t-BuONa (1.44 g, 15 mmol), Pd(dba)$_2$ (0.18 g, 0.2 mmol), and (t-Bu)$_3$P (0.04~0.06 g, 0.2~0.3 mmol) were added thereto. The reaction mixture was stirred at 80° C. for five hours. The reaction solution was extracted three times with ethylether (50 ml). The collected organic layer was dried over magnesium sulfate to evaporate a solvent, and the residue was purified by silica gel column chromatography to give intermediate H (2.3 g, yield: 63%). $^1$H NMR (CDCl$_3$, 400 MHz) δ (ppm) 8.23 (d, 1H), 7.74 (d, 1H), 7.46 (dt, 1H), 7.28 (d, 1H), 7.25 (d, 1H), 7.18 (dt, 2H), 7.08-7.01 (m, 6H), 6.75-6.71 (m, 1H), 6.57 (dd, 1H), 5.79 (s, 2H), 5.56 (s, 1H); $^{13}$C NMR (CDCl$_3$, 100 MHz) δ (ppm) 164.8, 159.4, 144/7, 139.6, 135.4, 134.2, 134.1, 129.3, 129.1, 128.8, 127.8, 126.1, 120.8, 119.9, 119.2, 119.1, 118.7, 116.8, 115.8, 115.2, 109.9, 109.7, 109.5, 103.1, 45.2.

Synthesis of Compound 33

Intermediate H (3.67 g, 10 mmol) and intermediate G (4.41 g, 11 mmol) were dissolved in toluene (50 ml), and t-BuONa (1.44 g, 15 mmol), Pd(dba)$_2$ (0.18 g, 0.2 mmol), and (t-Bu)$_3$P (0.04~0.06 g, 0.2~0.3 mmol) were added thereto. The reaction mixture was stirred at 90° C. for six hours. The reaction solution was extracted three times with ethylether (50 ml). The collected organic layer was dried over magnesium sulfate to evaporate a solvent, and the residue was purified by silica gel column chromatography to give compound 33 (3.71 g, yield: 58%). The structure of compound 33 was determined by $^1$H-NMR and $^{13}$C NMR: $^1$H-NMR (CDCl$_3$, 400 MHz) δ (ppm) 8.14 (d, 2H), 7.89 (d, 2H), 7.46 (dt, 2H), 7.36-7.28 (m, 4H), 7.19 (dt, 2H), 7.10-7.02 (m, 8H), 6.82 (d, 2H), 6.73 (dd, 2H), 6.64-5.99 (m, 1H), 5.79 (s, 4H), 5.68 (dd, 2H); $^{13}$C NMR (CDCl$_3$, 100 MHz) δ (ppm) 165.3, 160.2, 149.9, 143.7, 137.7, 137.3, 134.2, 134.1, 129.4, 129.0, 128.8, 126.1, 122.9, 122.8, 122.7, 121.2, 118.2, 116.8, 115.9, 115.2, 115.0, 111.5, 111.0, 108.5, 45.3.

Example 1

A 15 Ω/cm$^2$ ITO glass substrate (Corning, 1,200 Å) was cut into pieces of 50 mm×50 mm×0.7 mm in size, followed by ultrasonic cleaning in isopropyl alcohol and pure water (5 minutes for each), exposure to UV light for 30 minutes, and then ozone cleaning, to thereby form anodes. The anodes were placed in a vacuum deposition machine.

Compound 1 was vacuum-deposited to a thickness of 600 Å on the anodes to form hole injection layers. Then, a hole transport compound, 4,4'-bis[N-(1-naphthyl)-N-phenylamino]biphenyl (referred to as "NPB", hereinafter) was vacuum-deposited to a thickness of 300 Å on the hole injection layers to form hole transport layers.

A known blue fluorescent host, IDE215 (Idemitsu), and a known blue fluorescent dopant, IDE118 (Idemitsu) (weight ratio of 98:2) were co-deposited to a thickness of 200 Å on the hole transport layers to form emitting layers.

Next, Alq3 was deposited to a thickness of 300 Å on the emitting layers to form electron transport layers. LiF (10 Å, electron injection layers), which is halogenated alkaline metal, and Al (3000 Å, cathodes) were deposited on the electron transport layers to form LiF/Al electrodes, thereby completing the manufacture of organic light-emitting devices.

The organic light-emitting devices exhibited a driving voltage of 7.68V at a current density of 100 mA/cm$^2$, high brightness of 6,567 cd/m$^2$, color coordinates of (0.144, 0.241), and an emission efficiency of 6.57 cd/A.

Example 2

Organic light-emitting devices were manufactured in the same manner as in Example 1 except that hole injection layers were formed using compound 3 instead of compound 1.

The organic light-emitting devices exhibited a driving voltage of 7.92V at a current density of 100 mA/cm$^2$, brightness of 7,175 cd/m$^2$, color coordinates of (0.145, 0.245), which is almost the same as that of the organic light-emitting devices manufactured in Example 1, and a high emission efficiency of 7.18 cd/A.

Example 3

Organic light-emitting devices were manufactured in the same manner as in Example 1 except that hole injection layers were formed using compound 6 instead of compound 1.

The organic light-emitting devices exhibited a driving voltage of 7.27 V at a current density of 100 mA/cm$^2$, brightness of 7,184 cd/m$^2$, color coordinates of (0.145, 0.235) which is almost the same as that of the organic light-emitting devices manufactured in Example 1, and a high emission efficiency of 7.18 cd/A.

Example 4

Organic light-emitting devices were manufactured in the same manner as in Example 1 except that hole injection layers were formed using compound 33 instead of compound 1.

The organic light-emitting devices exhibited a low driving voltage of 7.05V at a current density of 100 mA/cm$^2$, high brightness of 7,622 cd/m$^2$, color coordinates of (0.144, 0.232) which is almost the same as that of the organic light-emitting devices manufactured in Example 3, and a high emission efficiency of 7.62 cd/A.

Comparative Example 1

Organic light-emitting devices were manufactured in the same manner as in Example 1 except that hole injection layers were formed using IDE406 (Idemitsu) instead of compound 1.

The organic light-emitting devices exhibited a driving voltage of 7.85V at a current density of 100 mA/cm$^2$, brightness of 5,961 cd/m$^2$, color coordinates of (0.147, 0.235) which is almost the same as that of the organic light-emitting devices manufactured in Example 1, and an emission efficiency of 5.96 cd/A.

When using the compounds 1, 3, 6, and 33 as hole injection layer materials, the charge injection capability was enhanced, thereby decreasing the driving voltage at the same current, and the current efficiency was enhanced, thereby increasing the brightness.

The experimental results are summarized in Table 1 below.

TABLE 1

| Example | Driving voltage (V) | Current density (mA/cm$^2$) | Brightness (cd/m$^2$) | Current efficiency (cd/A) | Color coordinates (x, y) |
|---|---|---|---|---|---|
| Example 1 | 5.87 | 10 | 570 | 5.7 | 0.144, 0.246 |
|  | 7.68 | 100 | 6,567 | 6.57 | 0.144, 0.241 |
| Example 2 | 6.04 | 10 | 621 | 6.21 | 0.145, 0.252 |
|  | 7.92 | 100 | 7,175 | 7.18 | 0.145, 0.245 |

TABLE 1-continued

| Example | Driving voltage (V) | Current density (mA/cm$^2$) | Brightness (cd/m$^2$) | Current efficiency (cd/A) | Color coordinates (x, y) |
|---|---|---|---|---|---|
| Example 3 | 5.87 | 10 | 684 | 6.84 | 0.146, 0.241 |
|  | 7.27 | 100 | 7,184 | 7.18 | 0.145, 0.235 |
| Example 4 | 5.35 | 10 | 708 | 7.08 | 0.144, 0.238 |
|  | 7.05 | 100 | 7,622 | 7.62 | 0.144, 0.232 |
| Comparative Example 1 | 6.35 | 10 | 567 | 5.67 | 0.148, 0.243 |
|  | 7.85 | 100 | 5,961 | 5.96 | 0.147, 0.235 |

When comparing the organic light-emitting devices employing the compounds of Examples 1-4 and the known IDE406, all of the organic light-emitting devices employing the compounds of Examples 1-4 exhibited I-V-L characteristics that were better than or equal to those of the organic light-emitting devices employing IDE406. The organic light-emitting devices manufactured in Examples 1-4 exhibited higher efficiency and brightness. In particular, the organic light-emitting devices employing the compound 33 exhibited an about 1V lower driving voltage, higher efficiency, and higher brightness than the organic light-emitting devices manufactured in Comparative Example 1. Meanwhile, the organic light-emitting devices manufactured in Examples 1-4 exhibited almost the same color coordinates and lifetime characteristics, compared with the organic light-emitting devices manufactured in Comparative Example 1.

When using compounds of Formula 1 as hole injection layer materials, it is possible to manufacture organic light-emitting devices with a low driving voltage, high efficiency, high brightness, and long lifetime, by virtue of good hole injection and transport capabilities of the compounds.

As described above, a fluorine-containing compound according to aspects of the present invention has good electrical characteristics and charge transport capability, and thus, is useful as a hole injection material, a hole transport material, and/or an emitting material for fluorescent or phosphorescent devices capable of producing light of a full spectrum of colors, including red, green, blue, and white. Thus, the fluorine-containing compound can be used to produce organic light-emitting devices with high efficiency, a low driving voltage, high brightness, and long lifetime.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A fluorine-containing compound represented by Formula 1 below:

<Formula 1>

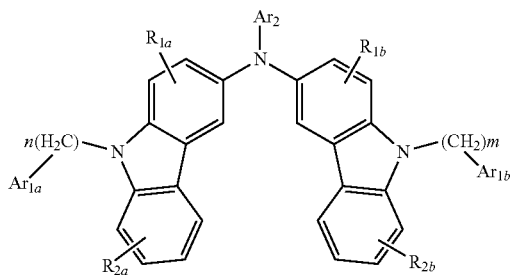

wherein $R_{1a}$, $R_{1b}$, $R_{2a}$, and $R_{2b}$ are each independently a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 aryloxy group, a substituted or unsubstituted C4-C30 heteroaryl group, a substituted or unsubstituted C6-C30 condensed polycyclic group, a hydroxy group, halogen, a cyano group, or a substituted or unsubstituted amino group, and adjacent groups selected from $R_{1a}$, $R_{1b}$, $R_{2a}$, and $R_{2b}$ may join together to form a saturated or unsaturated carbon ring;

n and m are each independently an integer of 0 to 5;

$Ar_{1a}$ and $Ar_{1b}$ are each independently selected from structures represented in Formula 2 below:

<Formula 2>

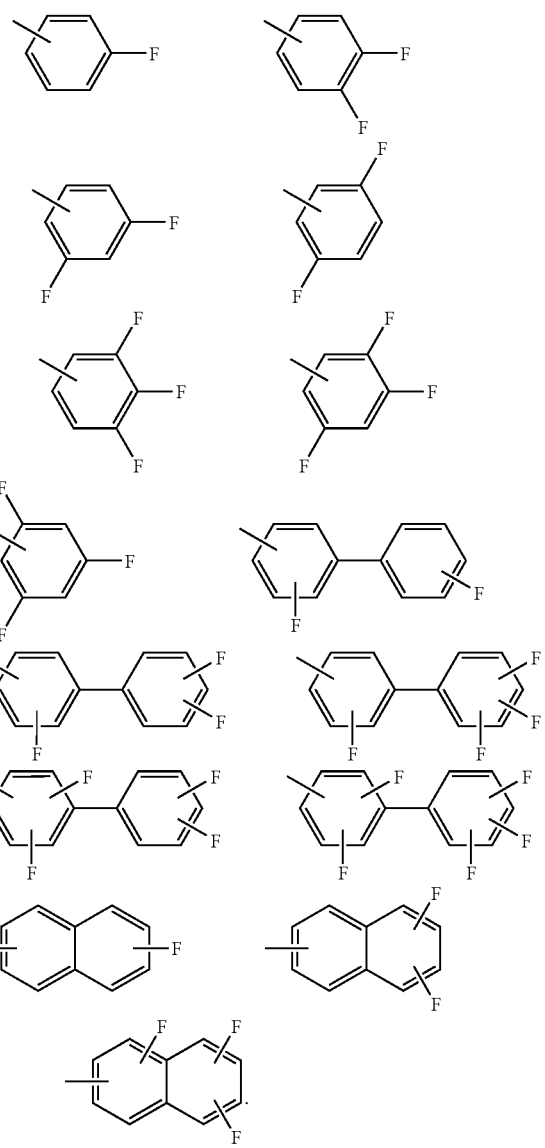

$Ar_2$ is a substituted or unsubstituted C6-C30 aryl group or a substituted or unsubstituted C2-C30 heteroaryl group.

2. The fluorine-containing compound of claim 1, wherein $Ar_2$ is one selected from the group consisting of a phenyl group, a C1-C5 alkylphenyl group, a C1-C5 alkoxyphenyl group, a cyanophenyl group, a phenoxyphenyl group, a halophenyl group, a naphthyl group, a C1-C5 alkylnaphthyl group, a C1-C5 alkoxynaphthyl group, a cyanonaphthyl group, a halonaphthyl group, a fluorenyl group, a carbazolyl group, a C1-C5 alkylcarbazolyl group, a biphenyl group, a C1-C5 alkylbiphenyl group, a C1-C5 alkoxybiphenyl group, and a pyridyl group.

3. The fluorine-containing compound of claim 1, wherein Ar₂ is selected from the group consisting of a phenyl group, an ethylphenyl group, an ethylbiphenyl group, an o-, m-, or p-fluorophenyl group, a dichlorophenyl group, a dicyanophenyl group, a trifluoromethoxyphenyl group, an o-, m-, or p-tolyl group, a mesytyl group, a phenoxyphenyl group, a dimethylphenyl group, a (N,N'-dimethyl)aminophenyl group, a (N,N'-diphenyl)aminophenyl group, a pentalenyl group, a naphthyl group, a methylnaphthyl group, an anthracenyl group, an azulenyl group, a heptalenyl group, an acetonaphthalenyl group, a fluorenyl group, an anthraquinolyl group, a phenanthryl group, a triphenylene group, a pentaphenyl group, a hexaphenyl group, and a carbazolyl group.

4. The fluorine-containing compound of claim 1, wherein m and n are independently 0, 1, or 2.

5. The fluorine-containing compound of claim 1, which is one selected from compounds 1-96 below:

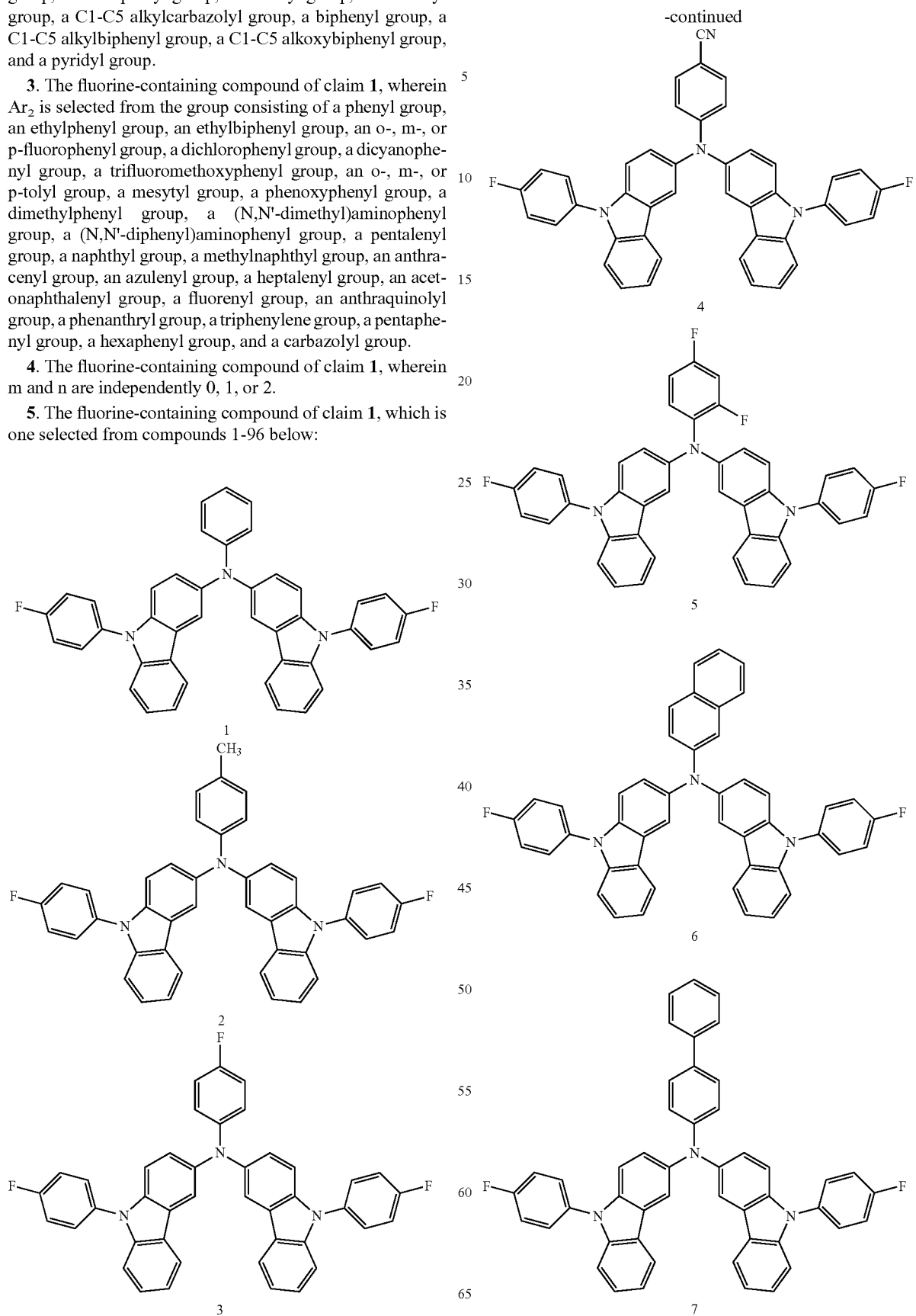

-continued
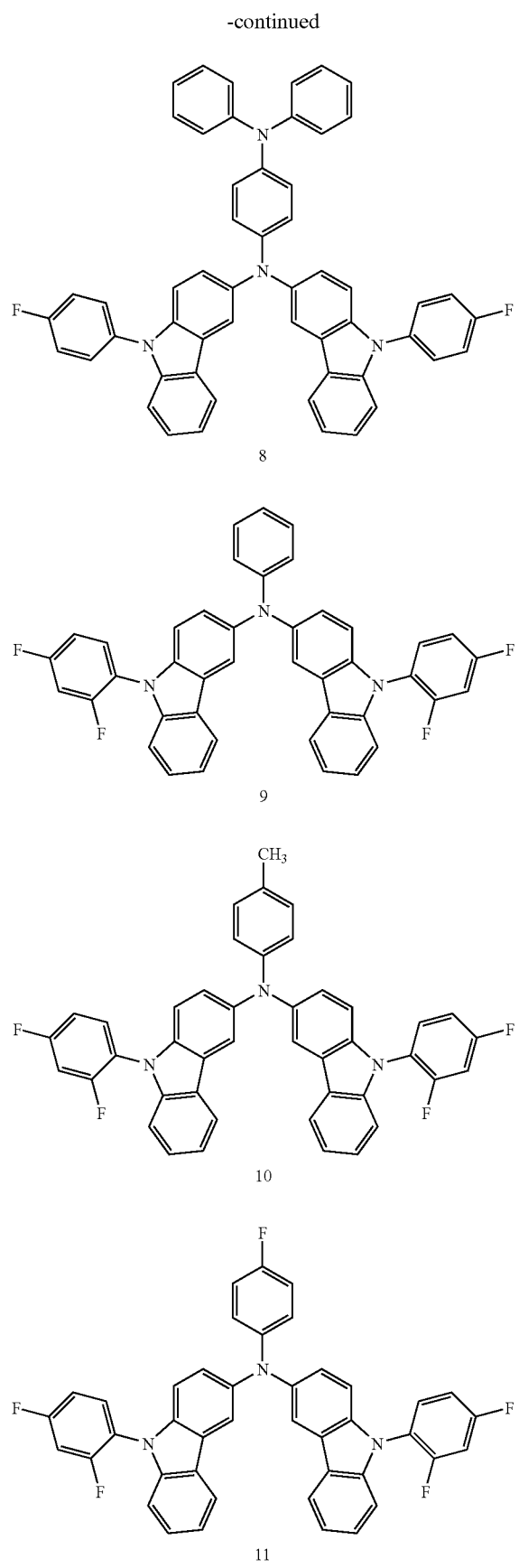
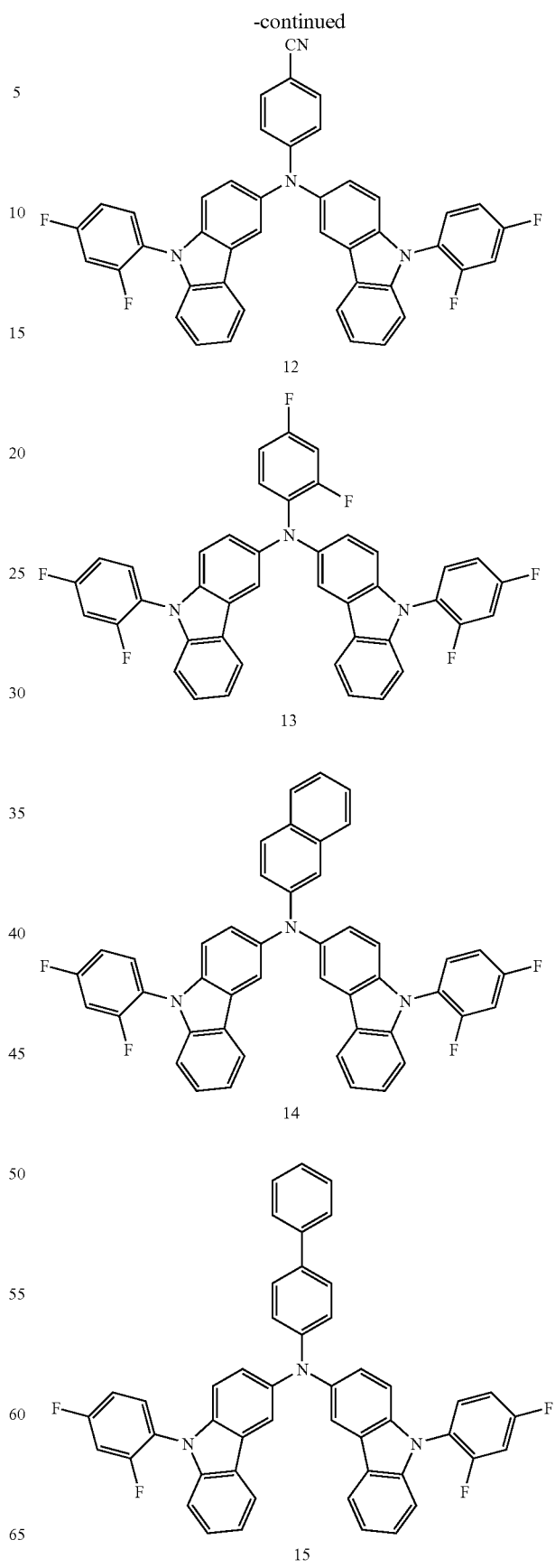

-continued
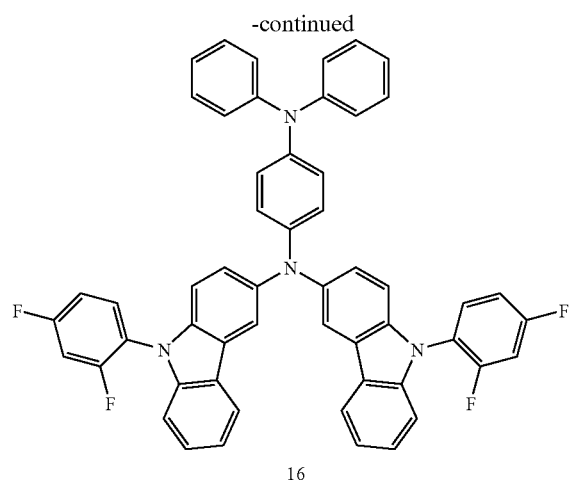
16
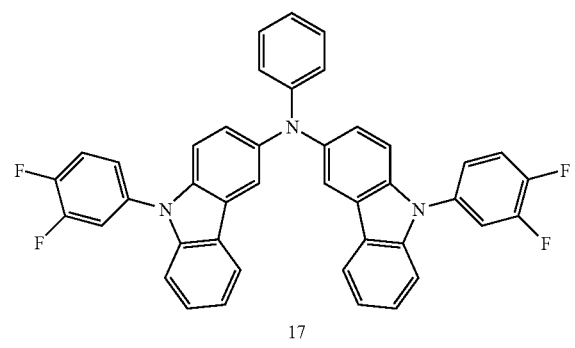
17
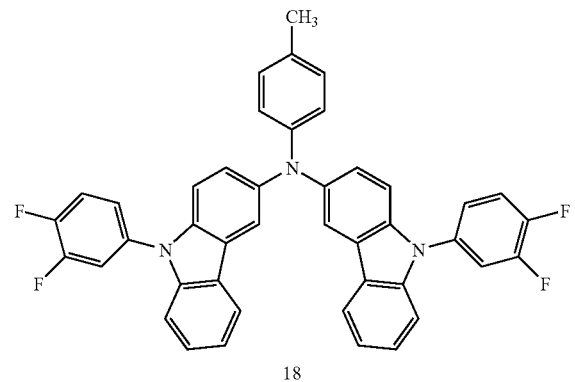
18
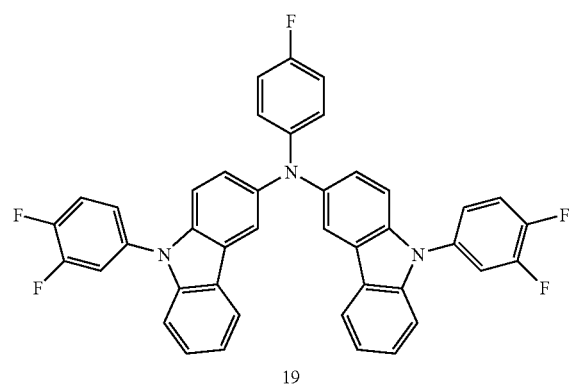
19
-continued
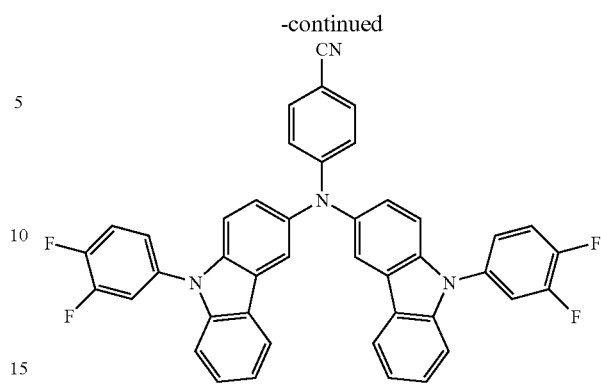
20
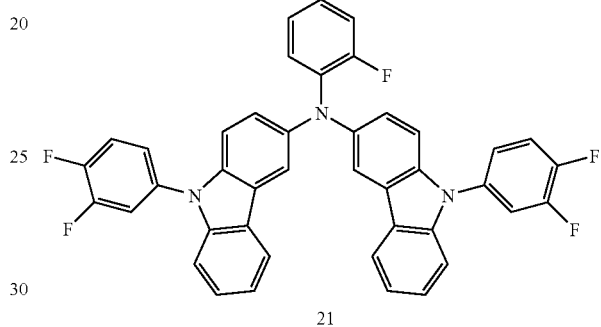
21
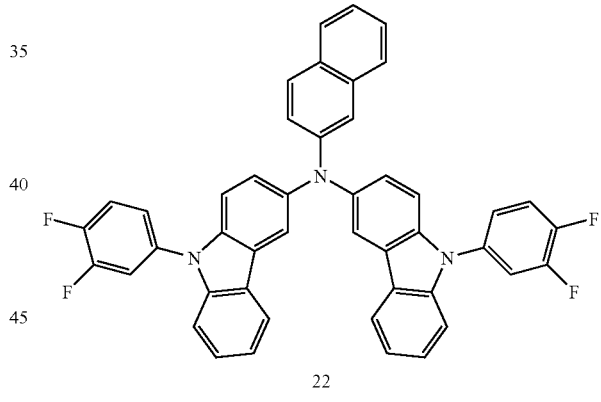
22
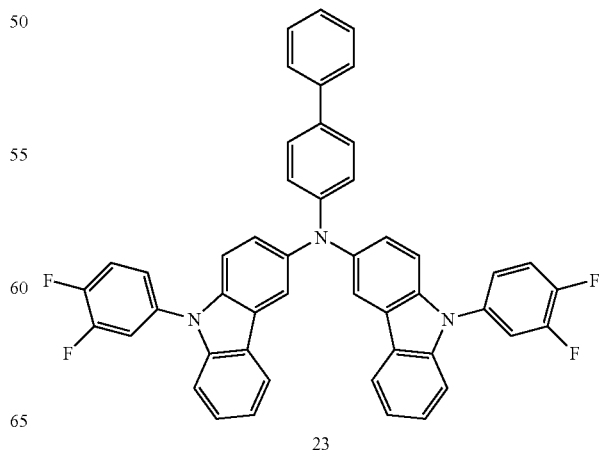
23

-continued
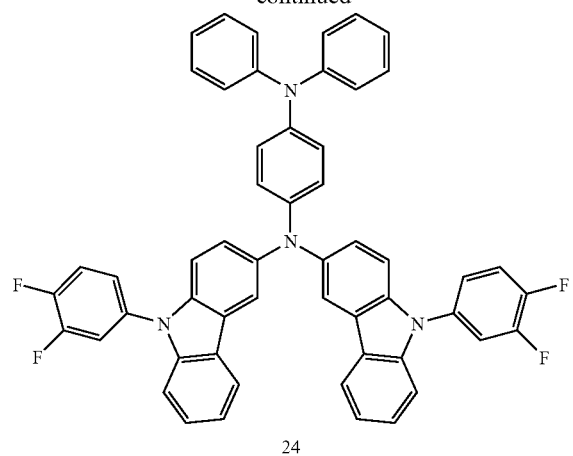
24
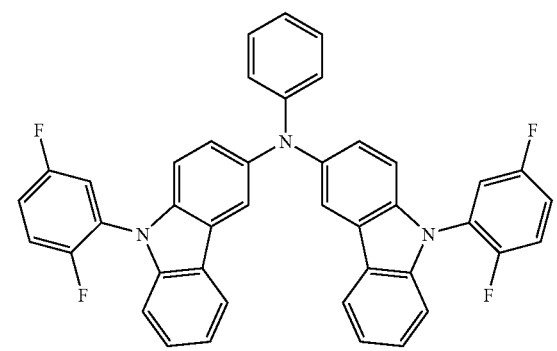
25
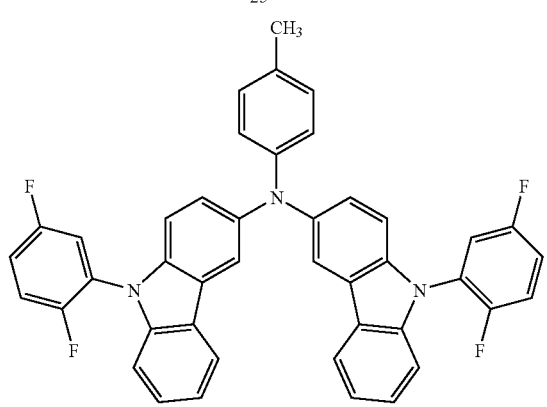
26
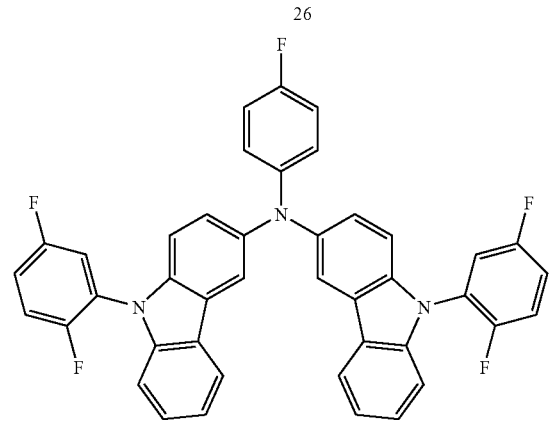
27
-continued
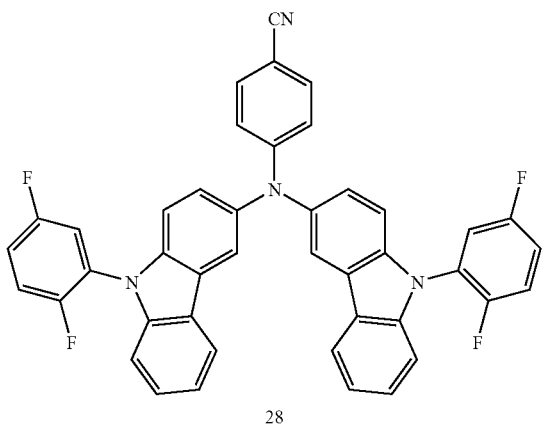
28
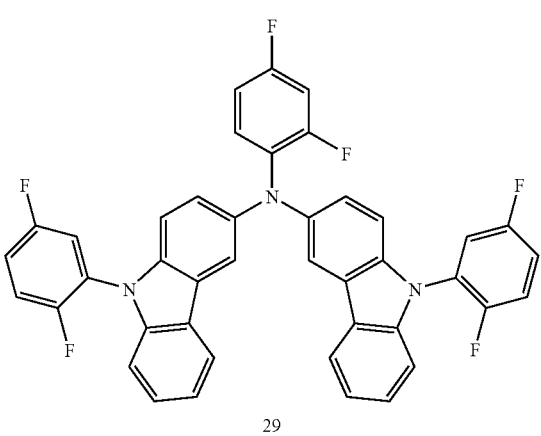
29
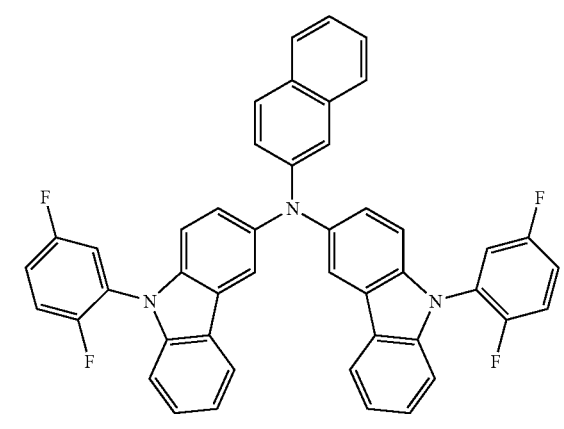
30

-continued
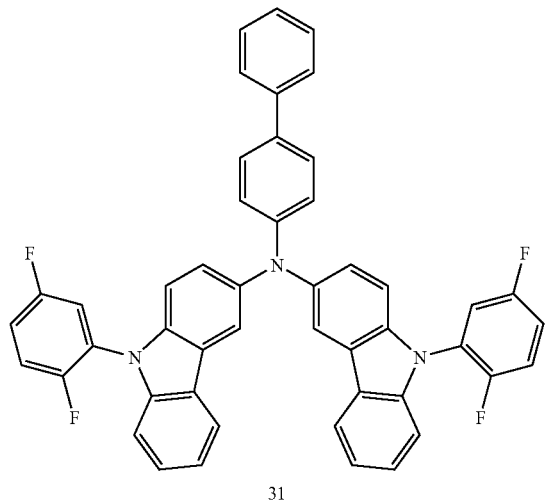
31
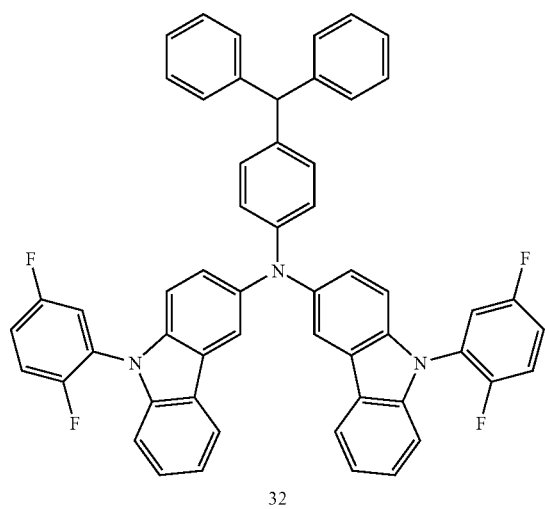
32
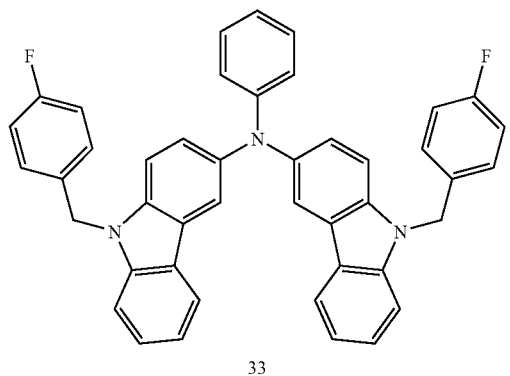
33
-continued
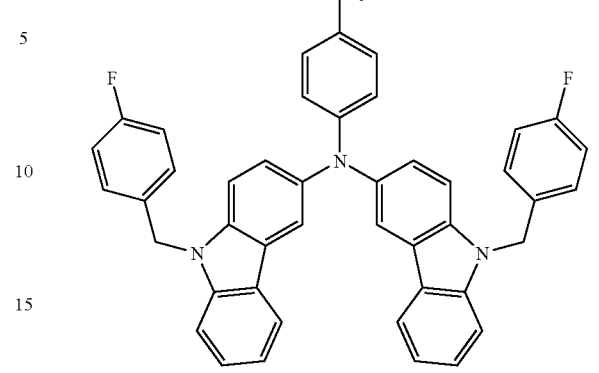
34
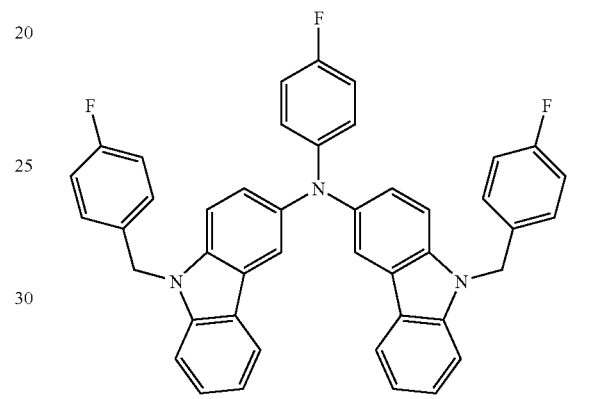
35
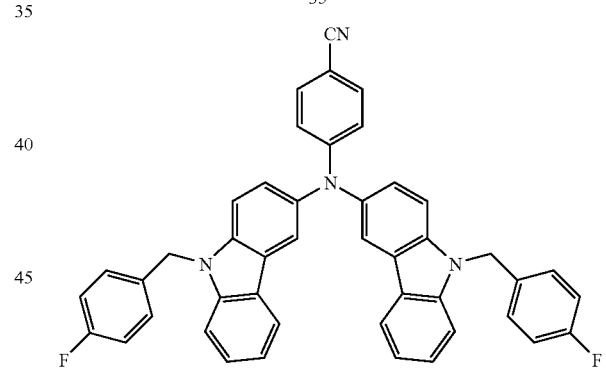
36
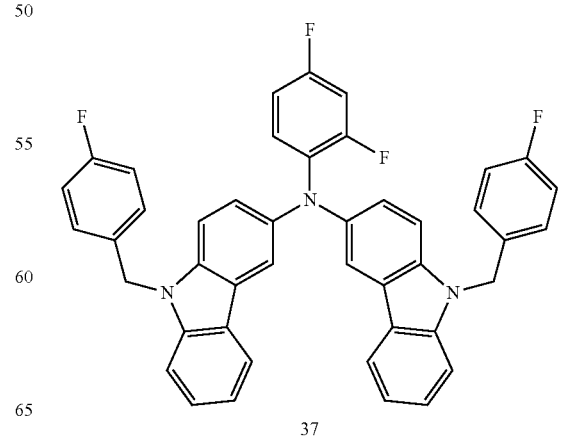
37

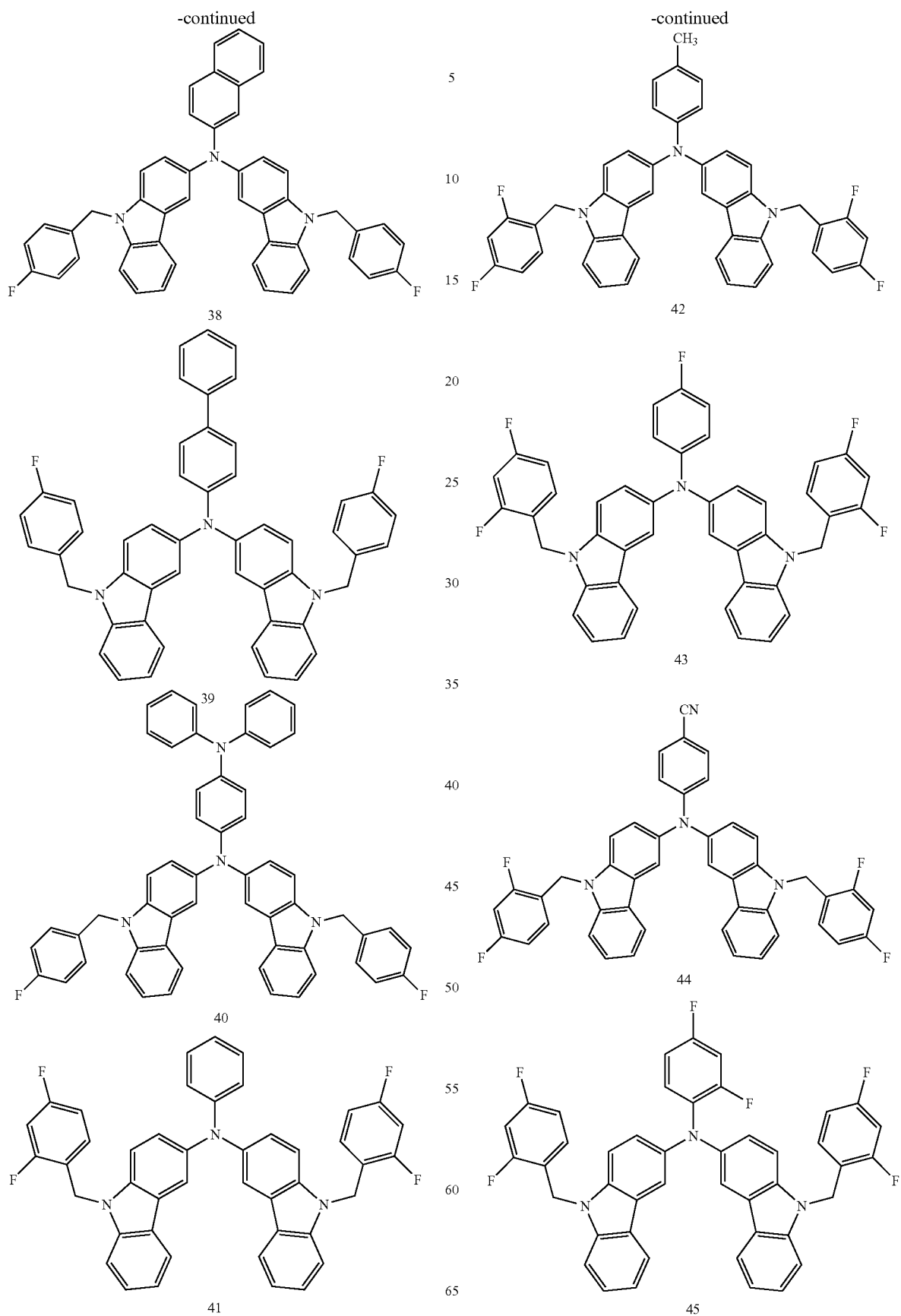

-continued
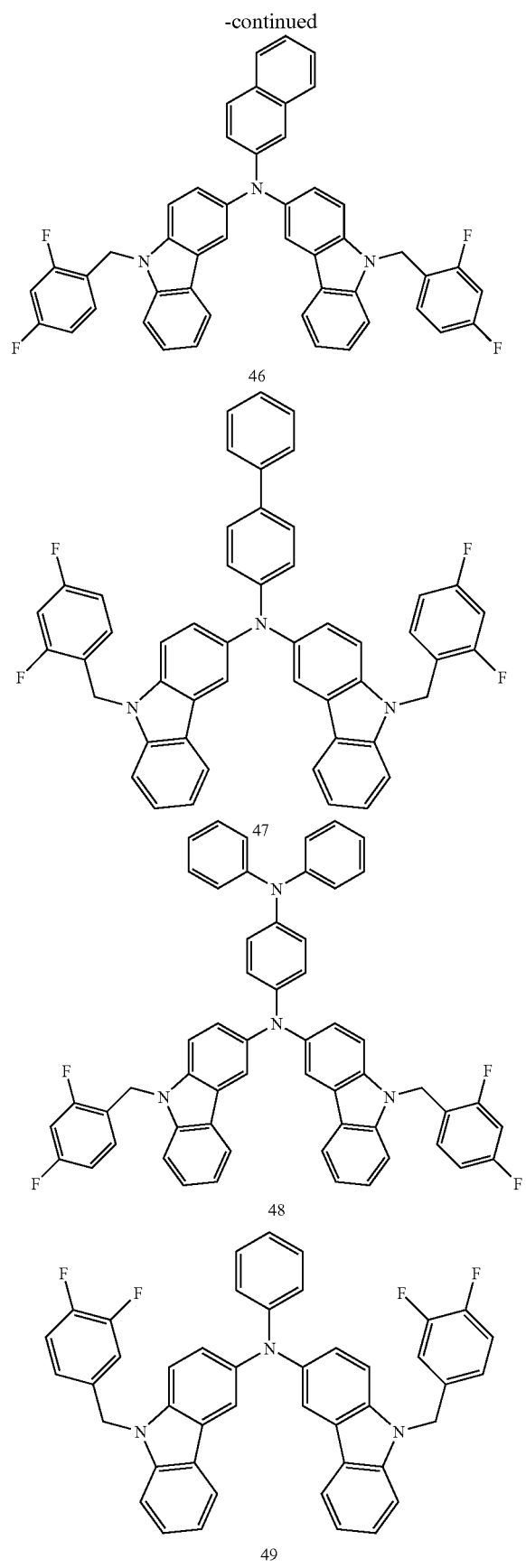
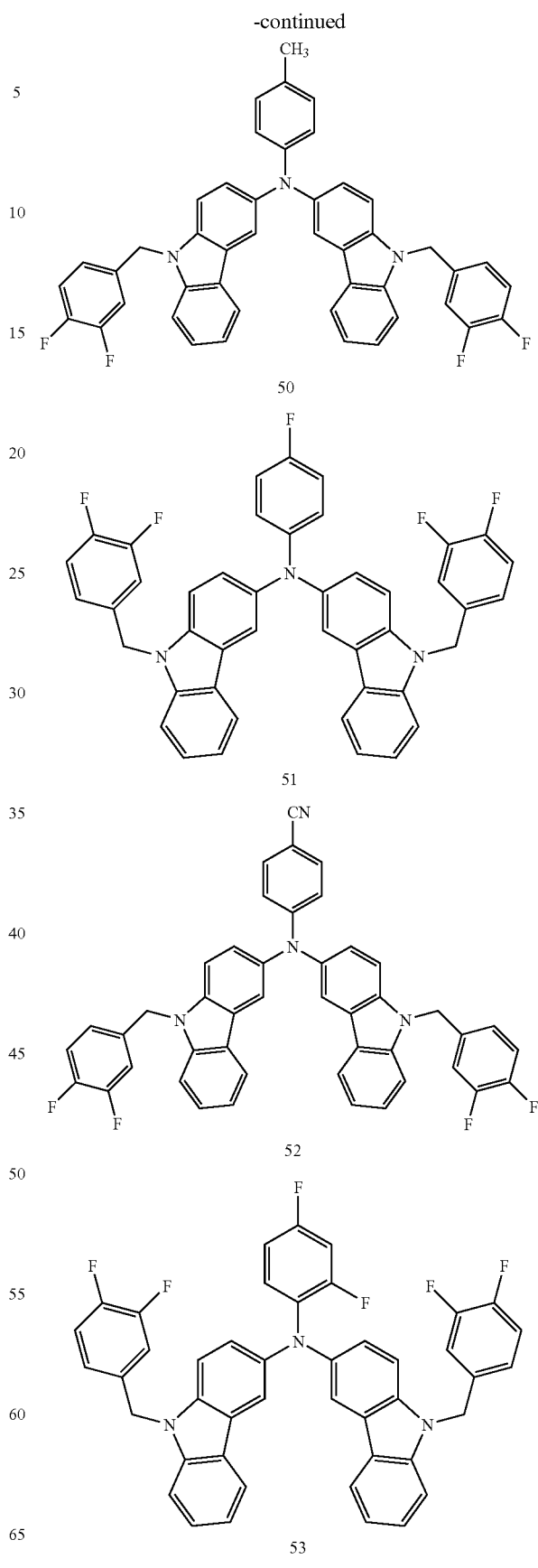

-continued
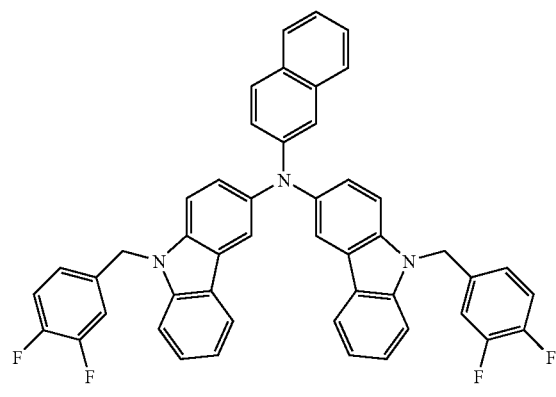
54
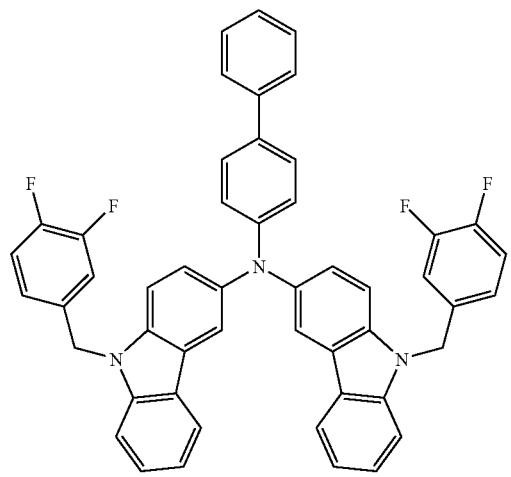
55
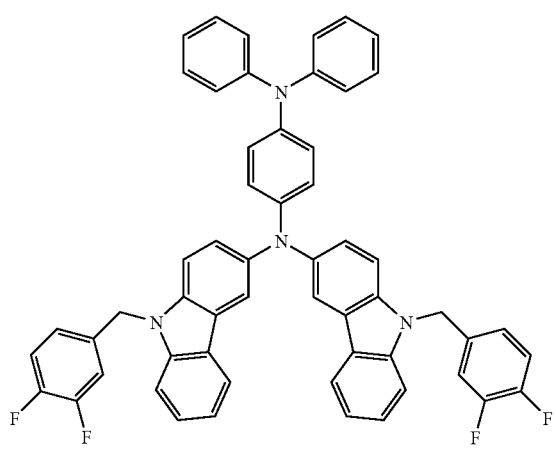
56
-continued
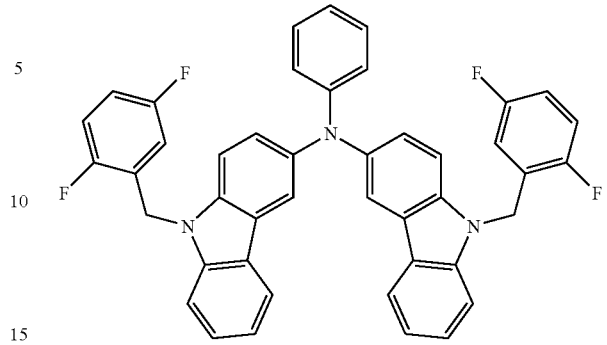
57
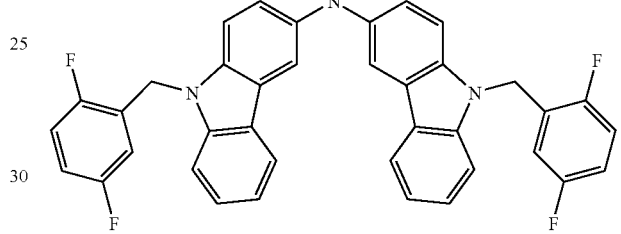
58
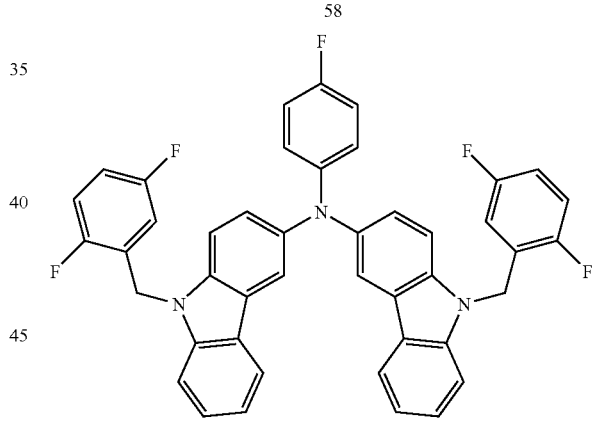
59
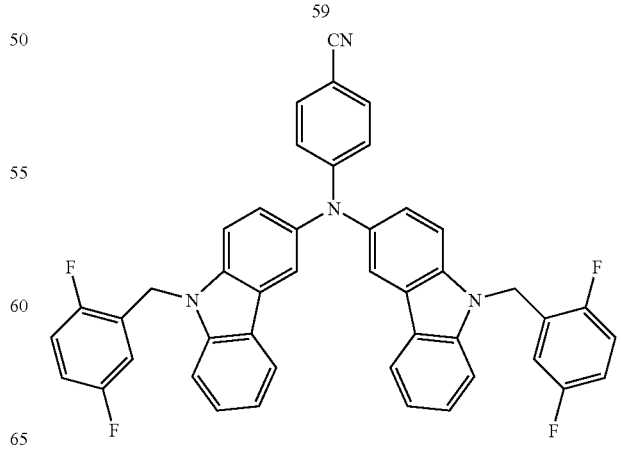
60

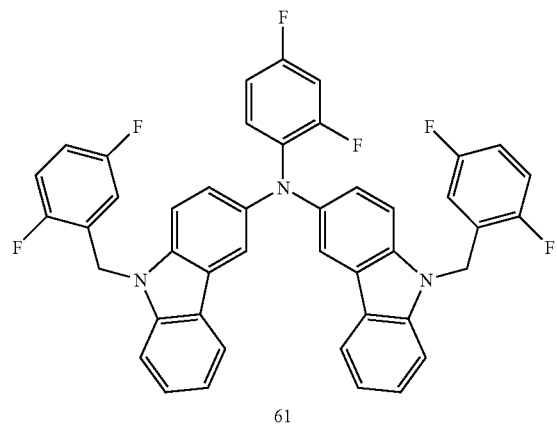
61
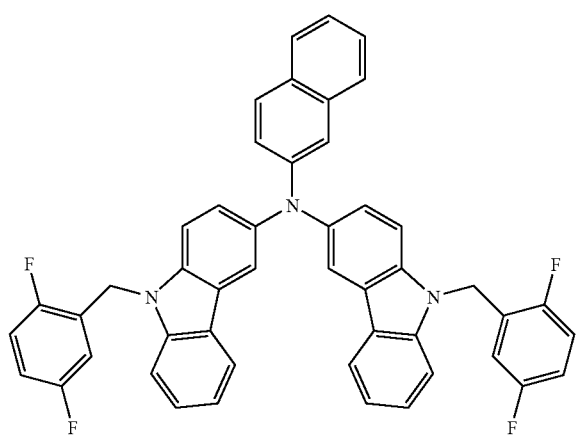
62
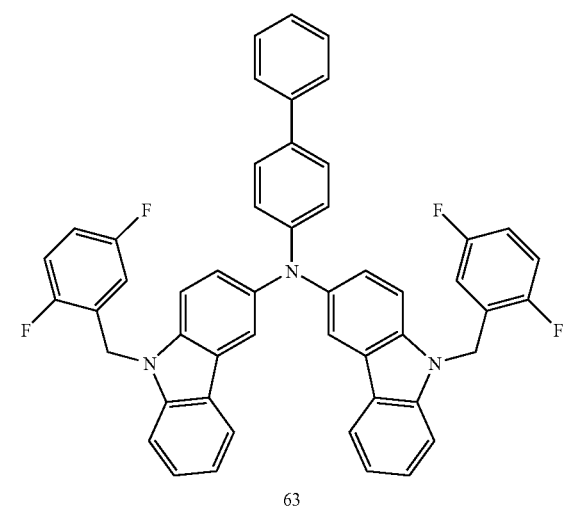
63
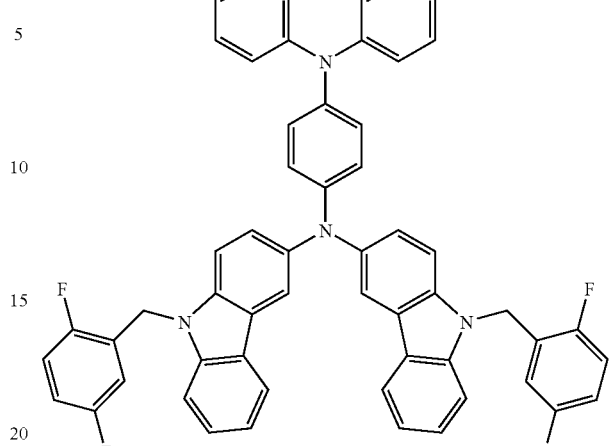
64
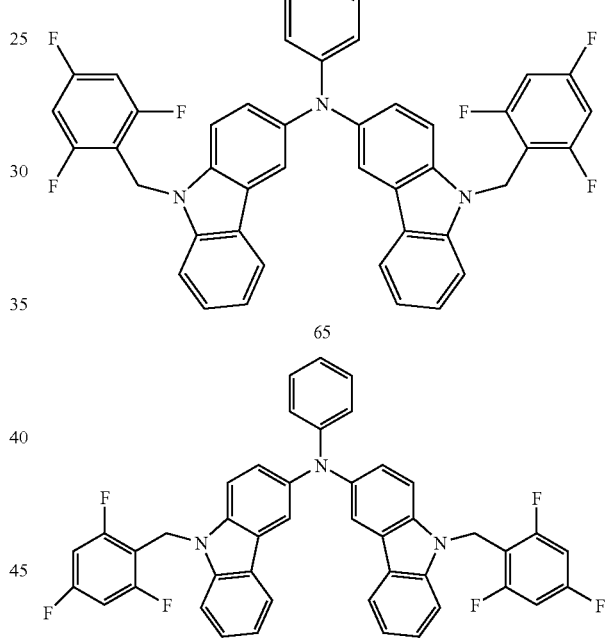
65
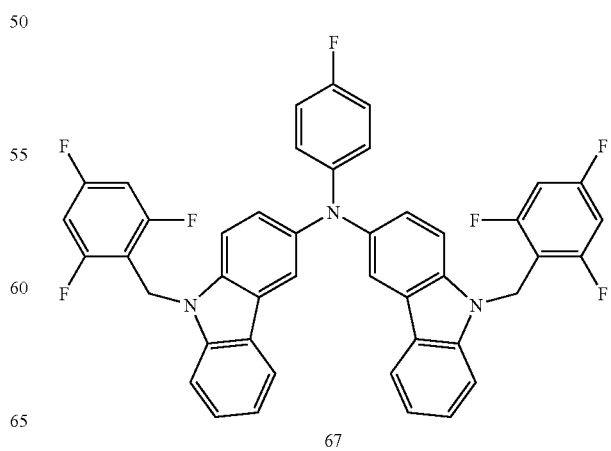
66
67

-continued
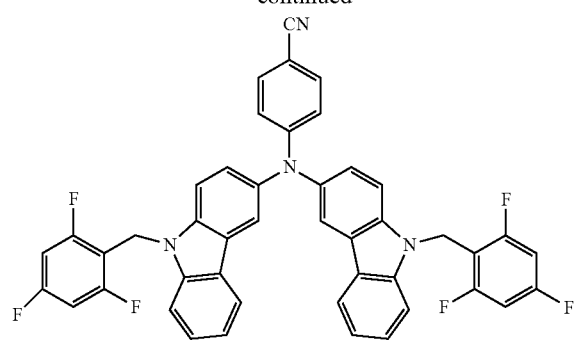

-continued
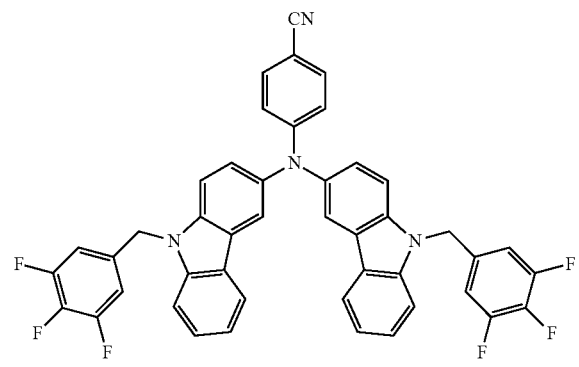
76
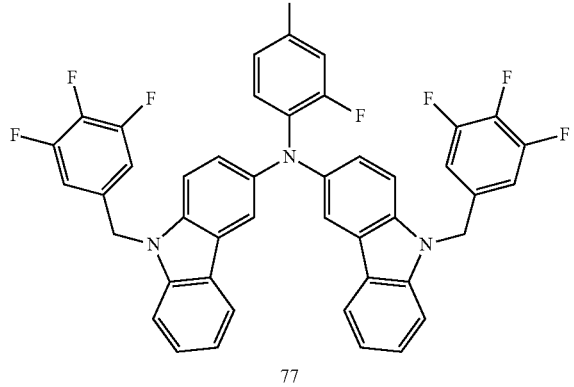
77
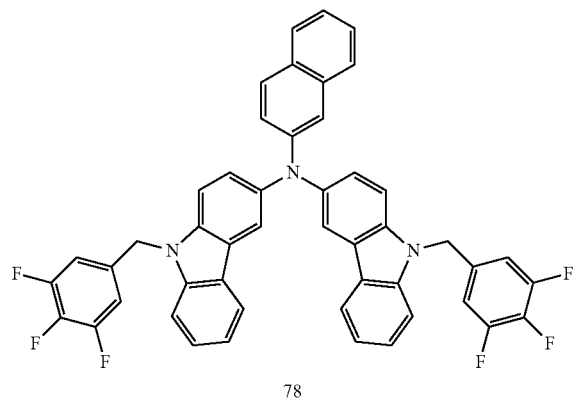
78
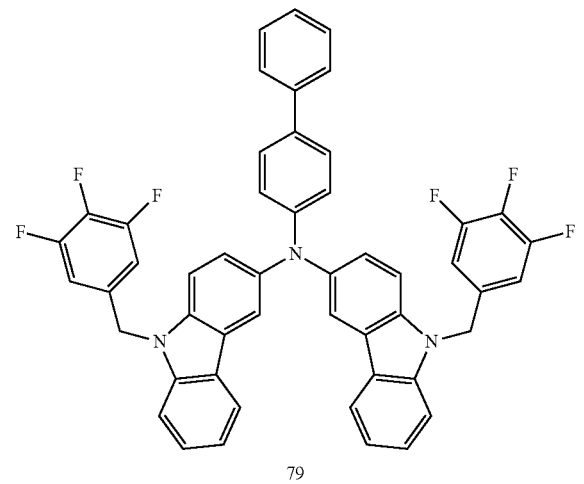
79
-continued
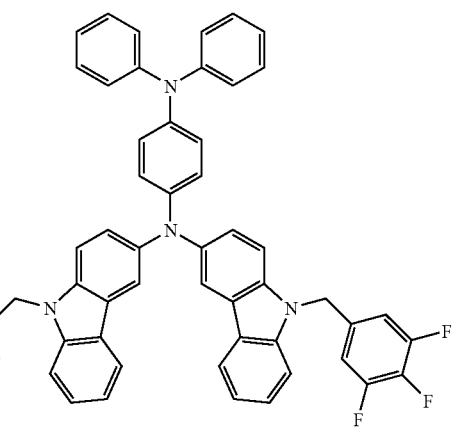
80
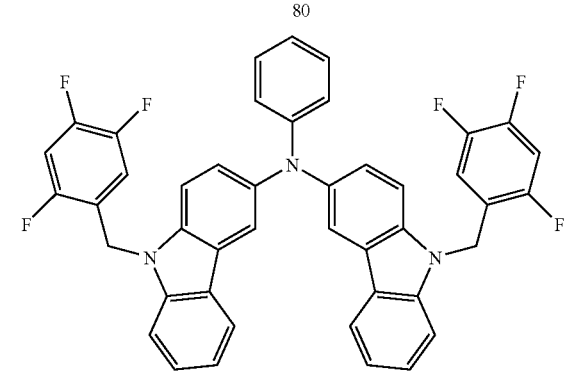
81
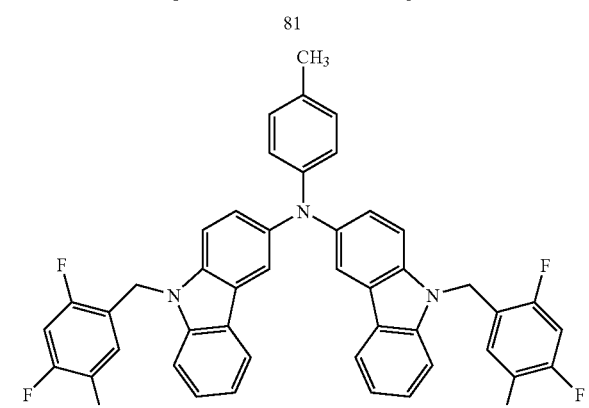
82
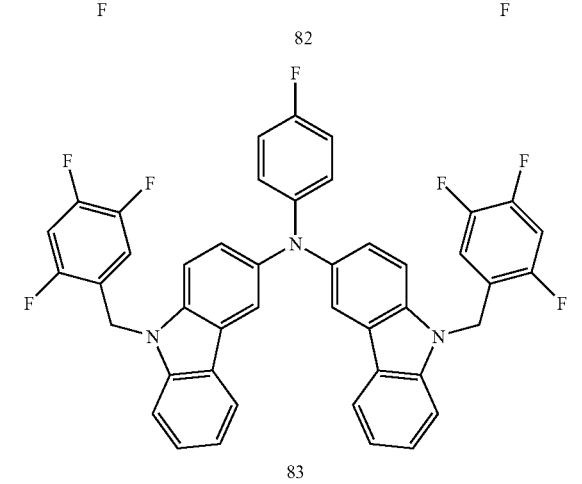
83

-continued
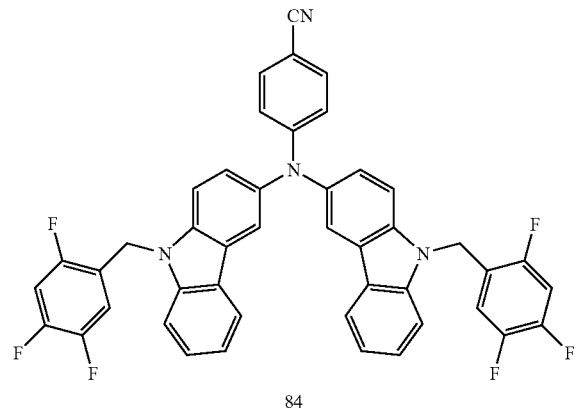
84
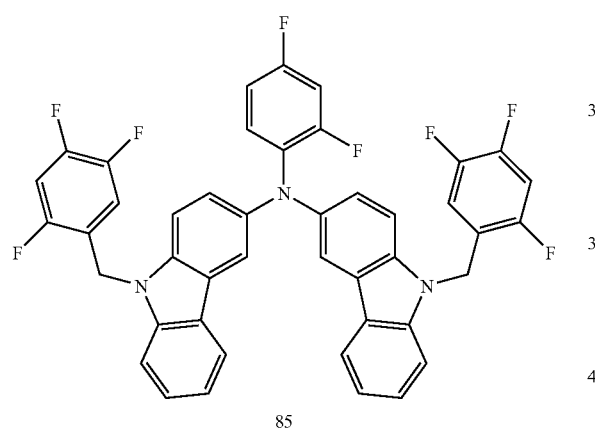
85
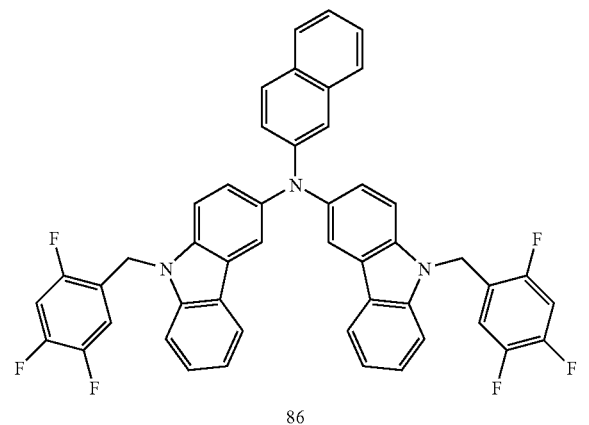
86
-continued
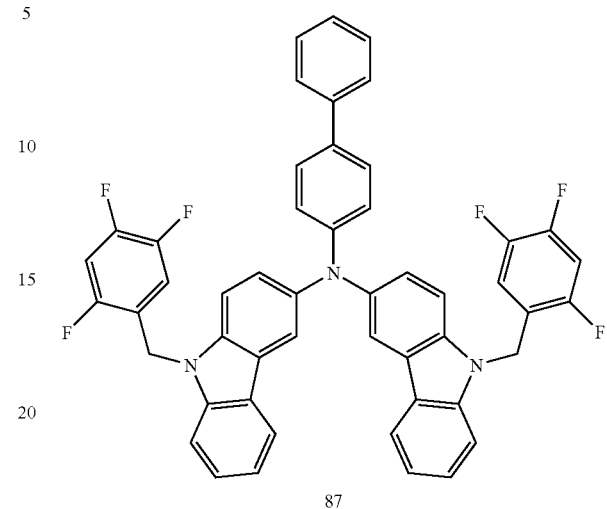
87
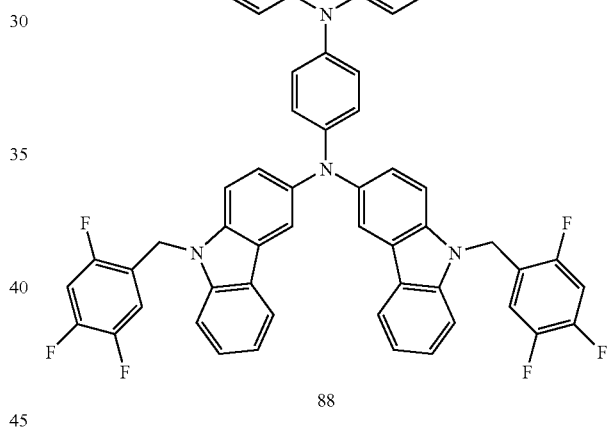
88
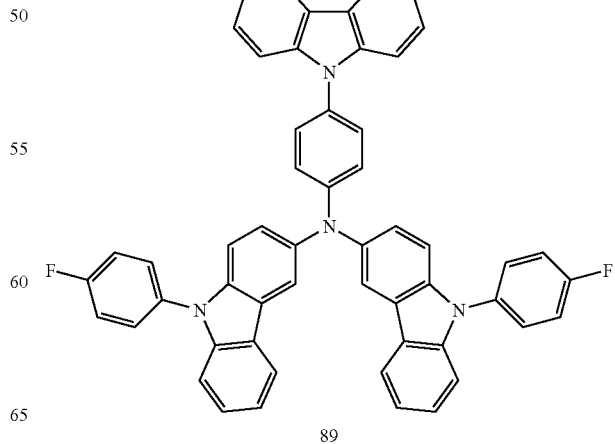
89

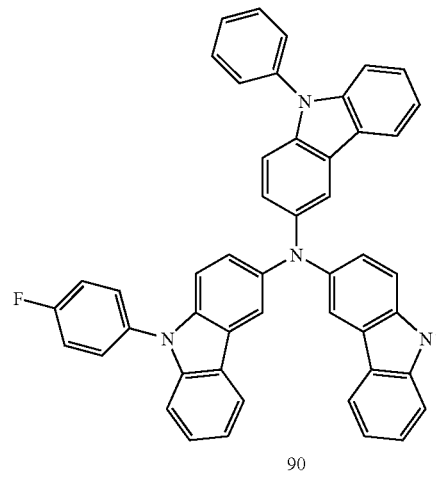
90
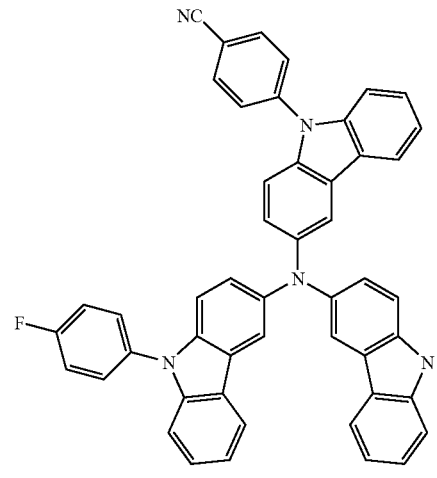
92
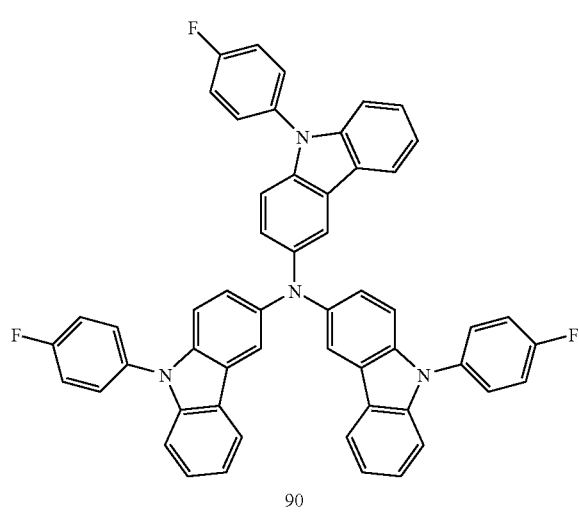
90
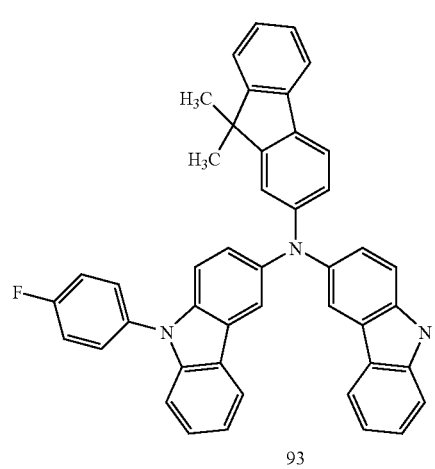
93
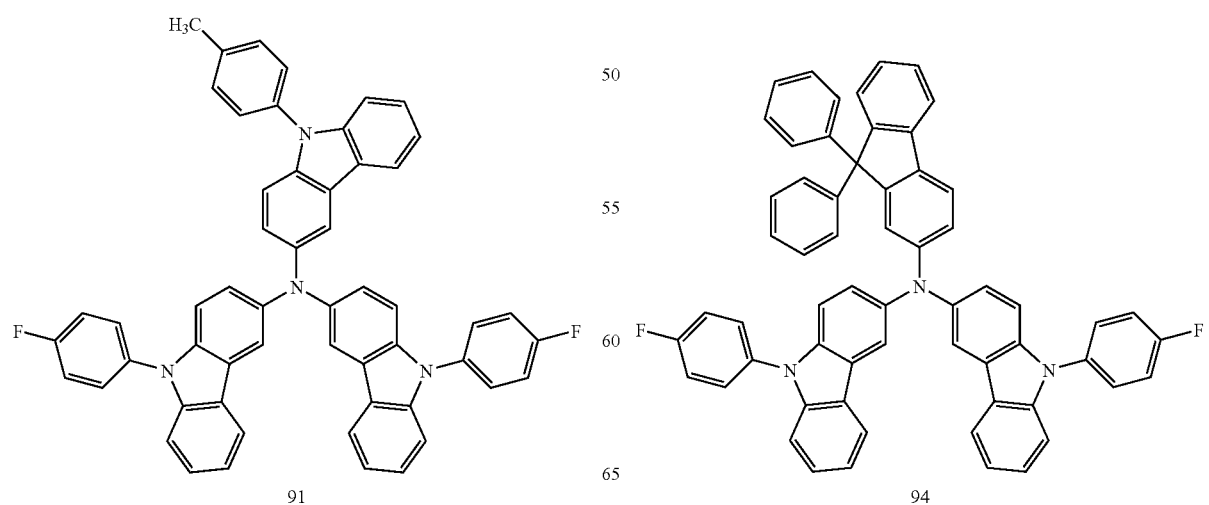
91
94

-continued

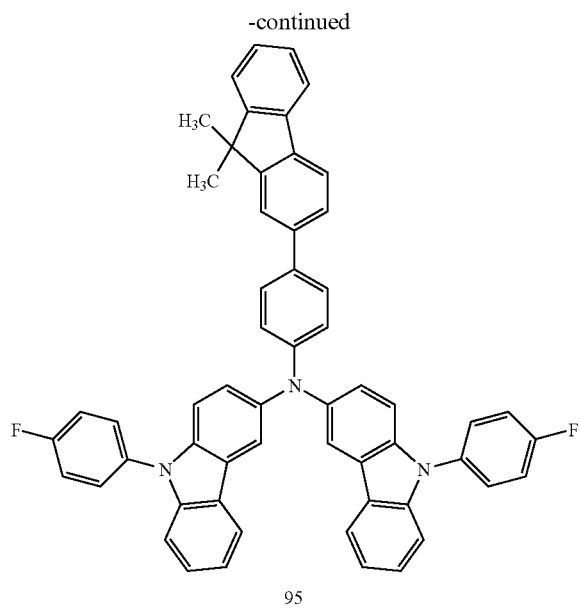

95

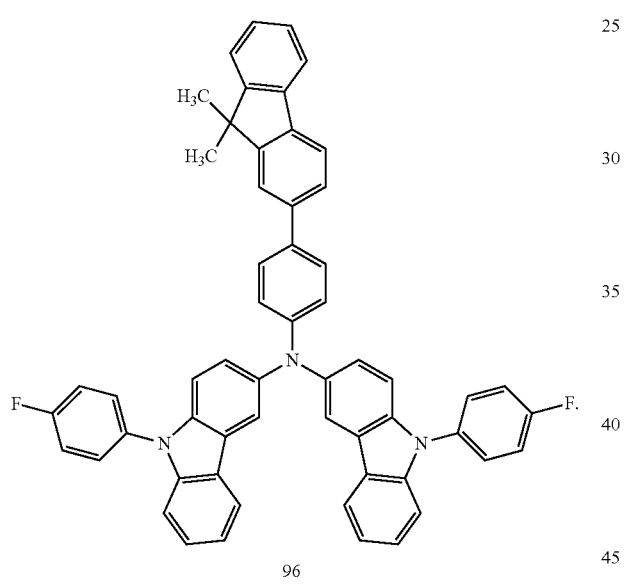

96

6. The fluorine-containing compound of claim 1, which is one of compounds 1, 3, 6, and 33 below:

1

-continued

3

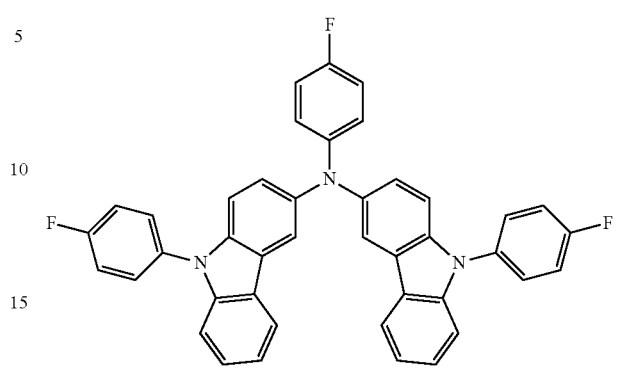

6

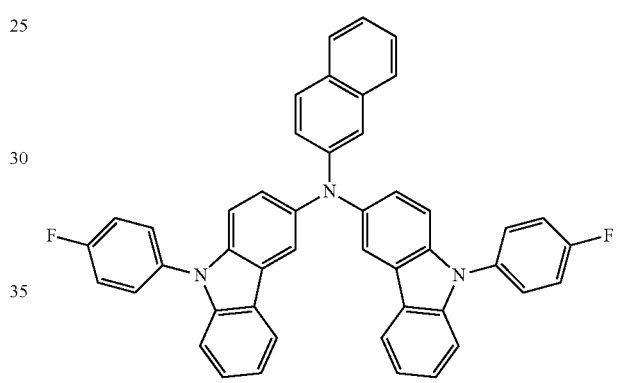

33

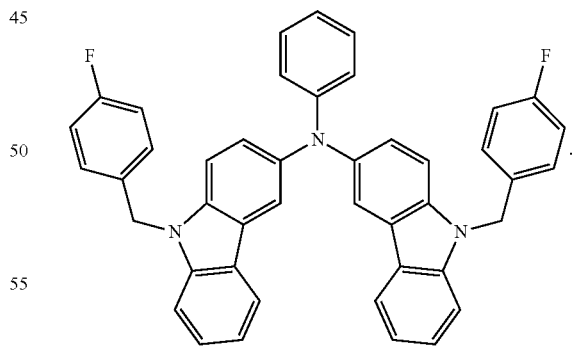

7. An organic light-emitting device comprising:
  a first electrode;
  a second electrode; and
  one or more organic layers interposed between the first electrode and the second electrode, wherein at least one of the one or more organic layers comprises a fluorine-containing compound represented by Formula 1 below:

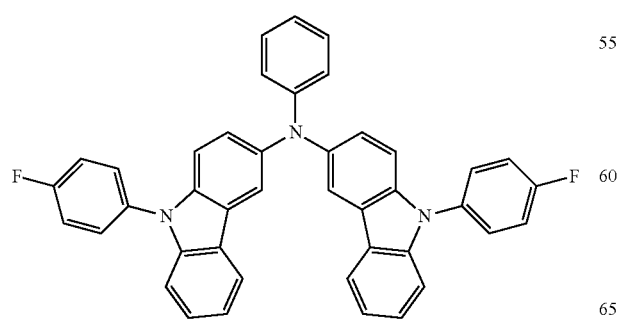

<Formula 1>

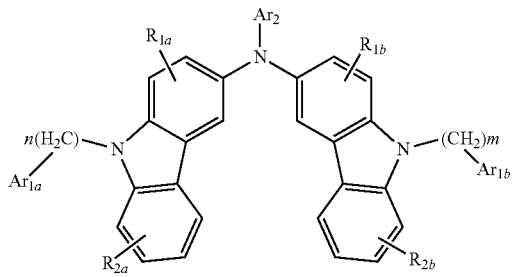

wherein $R_{1a}$, $R_{1b}$, $R_{2a}$, and $R_{2b}$ are each independently a hydrogen atom, a substituted or unsubstituted C1-C30 alkyl group, a substituted or unsubstituted C1-C30 alkoxy group, a substituted or unsubstituted C6-C30 aryl group, a substituted or unsubstituted C6-C30 aryloxy group, a substituted or unsubstituted C4-C30 heteroaryl group, a substituted or unsubstituted C6-C30 condensed polycyclic group, a hydroxy group, halogen, a cyano group, or a substituted or unsubstituted amino group, and adjacent groups selected from $R_{1a}$, $R_{1b}$, $R_{2a}$, and $R_{2b}$ may join together to form a saturated or unsaturated carbon ring;

n and m are each independently an integer of 0 to 5;

$Ar_{1a}$ and $Ar_{1b}$ are each independently selected from structures represented in Formula 2 below:

<Formula 2>

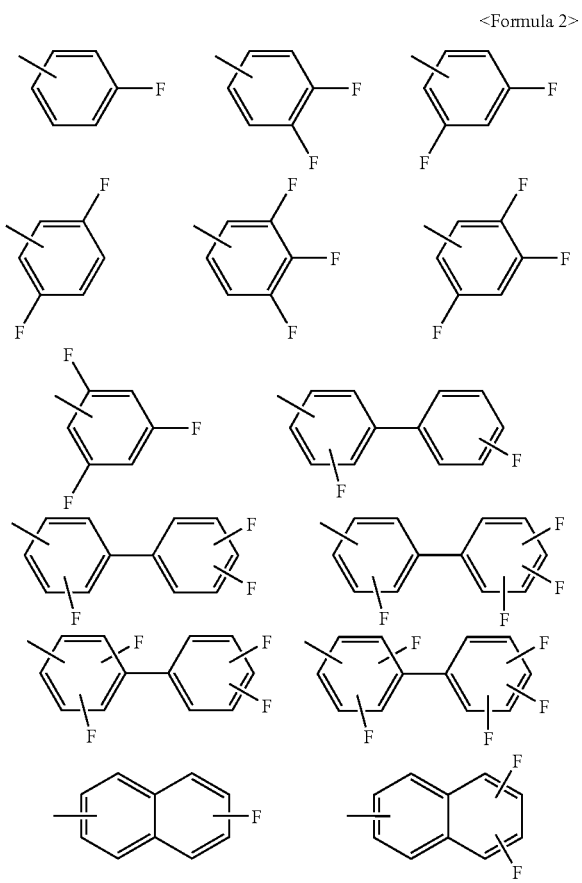

-continued

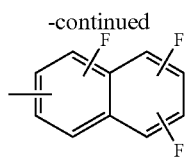

$Ar_2$ is a substituted or unsubstituted C6-C30 aryl group or a substituted or unsubstituted C2-C30 heteroaryl group.

8. The organic light-emitting device of claim 7, wherein $Ar_2$ is one selected from the group consisting of a phenyl group, a C1-C5 alkylphenyl group, a C1-C5 alkoxyphenyl group, a cyanophenyl group, a phenoxyphenyl group, a halophenyl group, a naphthyl group, a C1-C5 alkylnaphthyl group, a C1-C5 alkoxynaphthyl group, a cyanonaphthyl group, a halonaphthyl group, a fluorenyl group, a carbazolyl group, a C1-C5 alkylcarbazolyl group, a biphenyl group, a C1-C5 alkylbiphenyl group, a C1-C5 alkoxybiphenyl group, and a pyridyl group.

9. The organic light-emitting device of claim 7, wherein the organic layer comprising the fluorine-containing compound is a hole injection layer or a hole transport layer.

10. The organic light-emitting device of claim 9, wherein the organic layer comprising the fluorine-containing compound is a single layer having both hole injection and hole transport capabilities.

11. The organic light-emitting device of claim 7, wherein the organic layer comprising the fluorine-containing compound is a hole injection layer or a hole transport layer or a single layer having both hole injection and hole transport capabilities, and wherein the organic light-emitting device has one of the following structures:

first electrode/hole injection layer/emitting layer/second electrode;

first electrode/hole injection and transport layer/emitting layer/electron transport layer/second electrode;

first electrode/hole injection layer/hole transport layer/emitting layer/electron transport layer/second electrode;

first electrode/hole injection layer/hole transport layer/emitting layer/electron transport layer/electron injection layer/second electrode; or first electrode/hole injection layer/hole transport layer/emitting layer/hole blocking layer/electron transport layer/electron injection layer/second electrode.

12. The organic light-emitting device of claim 7, wherein the organic layer comprising the fluorine-containing compound is an emitting layer.

13. The organic light-emitting device of claim 12, wherein the emitting layer includes a phosphorescent or fluorescent material.

14. The organic light-emitting device of claim 13, wherein in the emitting layer, the fluorine-containing compound is a fluorescent or phosphorescent host.

15. An organic light-emitting device comprising a hole injection layer or a hole transport layer or a single layer having both hole injection and hole transport capabilities comprising the fluorine-containing compound of claim 1.

16. An organic light-emitting device comprising an emitting layer comprising the fluorine-containing compound of claim 1.

* * * * *